US011322235B2

(12) United States Patent
Sri Prakash

(10) Patent No.: US 11,322,235 B2
(45) Date of Patent: May 3, 2022

(54) SYSTEMS AND METHODS FOR DIGITAL VACCINE

(71) Applicant: Bhargav Sri Prakash, San Francisco, CA (US)

(72) Inventor: Bhargav Sri Prakash, San Francisco, CA (US)

(*) Notice: Subject to any disclaimer, the term of this patent is extended or adjusted under 35 U.S.C. 154(b) by 129 days.

(21) Appl. No.: 16/653,937

(22) Filed: Oct. 15, 2019

(65) Prior Publication Data
US 2021/0110896 A1    Apr. 15, 2021

(51) Int. Cl.
| | | |
|---|---|---|
| *G16H 10/60* | (2018.01) | |
| *G16H 10/40* | (2018.01) | |
| *G16H 80/00* | (2018.01) | |
| *A63F 13/825* | (2014.01) | |
| *A61B 5/00* | (2006.01) | |
| *G16H 20/30* | (2018.01) | |
| *G16H 20/60* | (2018.01) | |
| *G06N 3/04* | (2006.01) | |

(52) U.S. Cl.
CPC .......... *G16H 10/60* (2018.01); *A61B 5/0015* (2013.01); *A63F 13/825* (2014.09); *G06N 3/0436* (2013.01); *G16H 10/40* (2018.01); *G16H 20/30* (2018.01); *G16H 20/60* (2018.01); *G16H 80/00* (2018.01)

(58) Field of Classification Search
CPC ........ G16H 10/60; G16H 10/40; G16H 80/00; G16H 20/30; G16H 20/60; G16H 50/50; A63F 13/825; A63F 13/67; A63F 13/58; A61B 5/0015; G06N 3/0436
See application file for complete search history.

(56) References Cited

U.S. PATENT DOCUMENTS

| | | | |
|---|---|---|---|
| 2010/0251117 A1 | 9/2010 | Baughman et al. | |
| 2013/0280681 A1* | 10/2013 | Narayan | G09B 19/0092 434/127 |
| 2017/0020461 A1 | 1/2017 | Quinn et al. | |
| 2017/0024540 A1 | 1/2017 | Han et al. | |

FOREIGN PATENT DOCUMENTS

| | | | |
|---|---|---|---|
| KR | 10-20020008934 A | | 2/2002 |
| KR | 20030057476 A | * | 7/2003 |
| KR | 101917043 B1 | | 1/2019 |

OTHER PUBLICATIONS

Polytechnic students create fight video game to promote physical activity. Notimex. Jun. 20, 2017 (Year: 2017).*
PCT/US2020/055630—International Search Report and Written Opinion dated Feb. 2, 2021, 8 pages.
Padman, Rema, et.al., "An Exploratory Analysis of Game Telemetry from a Pediatric mHealth Intervention", 2017, 5 pages.

(Continued)

*Primary Examiner* — Linh Giang Le
(74) *Attorney, Agent, or Firm* — Haynes Beffel & Wolfold LLP; Sikander M. Khan

(57) ABSTRACT

We disclose a digital vaccine system which presents a user-driven avatar with tasks that test the avatar's physical fitness and food offerings at various stages. The avatar's appearance is responsive to the avatar's performance on the tasks and selection of the food offerings. The digital vaccine system uses deep learning systems to configure and update its parameters.

20 Claims, 20 Drawing Sheets

Digital Vaccine System

(56) References Cited

OTHER PUBLICATIONS

Bruce, Amanda S., et al., "Brain Responses to Food Logos in Obese and Healthy Weight Children", 2016, 8 pages.
Padman, Rema, et.al., "Mobile Game-Based Digital Vaccine for Reducing Risk of Lifestyle Diseases", Sep. 17, 2018, 2 pages.
Baylor College of Medicine, Obesity Week Poster, "A nutrition education mobile game impacts snack selection in middle school students", 1 page.
M.S. Swaminathan et. al "Criteria for 'Digital Vaccines'—a new category of nutrition literacy and behavior design intervention with evidence-backed improvements in health outcomes", 20 pages, not dated.
Stanford Medicine X, "The Impact of 'fooya!'—a nutrition education Mobile Health Game—on food choices in middle school residential campers at the 2014 ExxonMobil Bernard Harris Summer Science Camp", dated Sep. 25, 2015, 5 pages.
Hofstra University, Padman et al., "Mobile Game-based Digital Vaccine for Reducing Risk of Lifestyle Diseases", not dated, 1 page.
Obesity Week, Multiple Abstracts, dated 2014, 806 pages.
Kato-Lin et al., "Impact of Artificial Intelligence-Enabled Mobile Gaming on Pediatric Health Risk Reduction Behavior", Journal for the American Medical Informatics Association, 22 pages.

\* cited by examiner

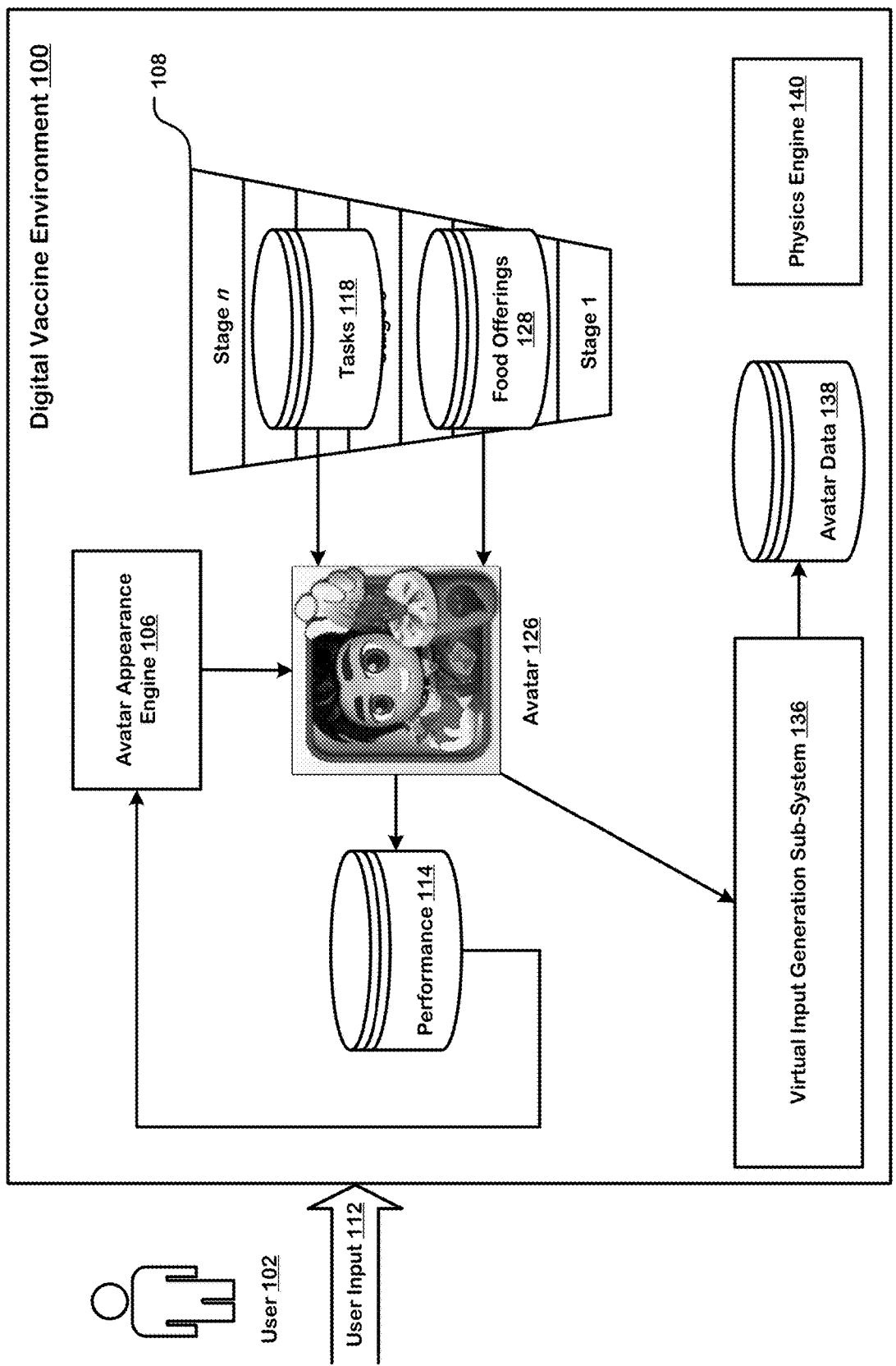
FIG. 1 – Digital Vaccine System

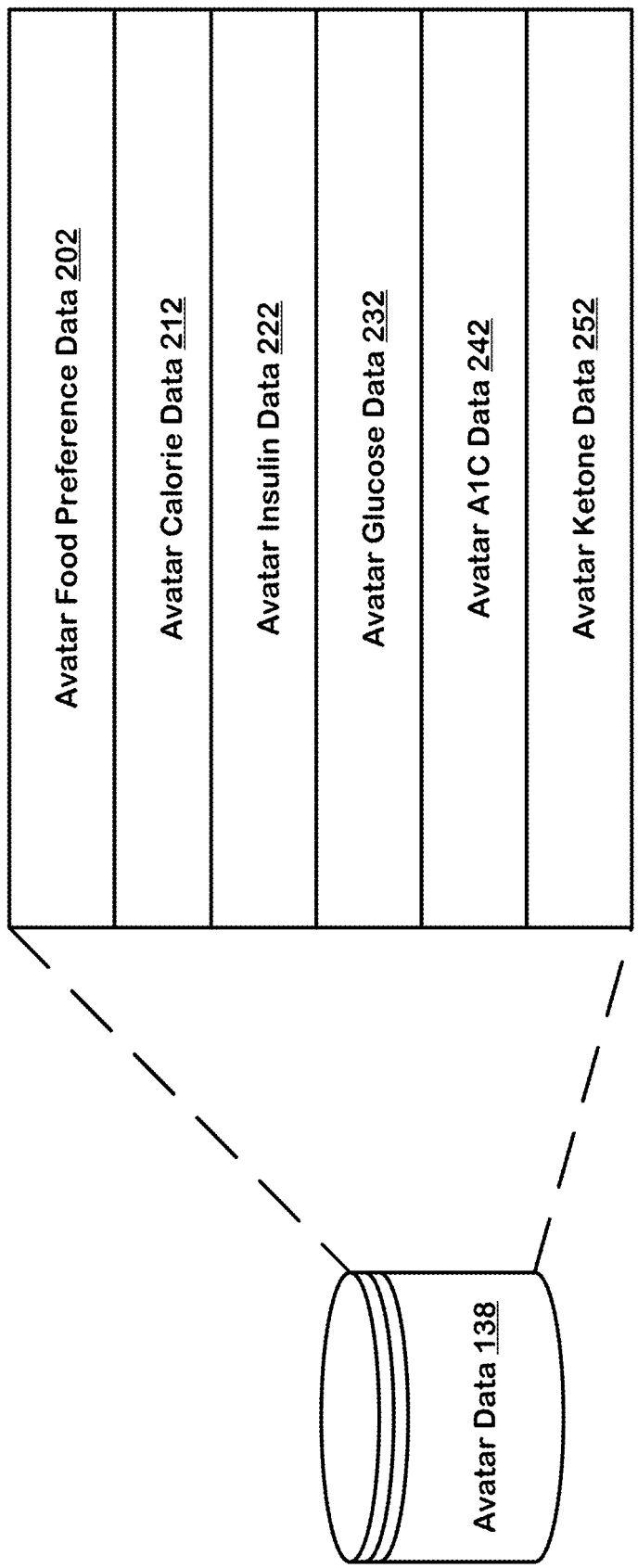
FIG. 2 – Avatar Data

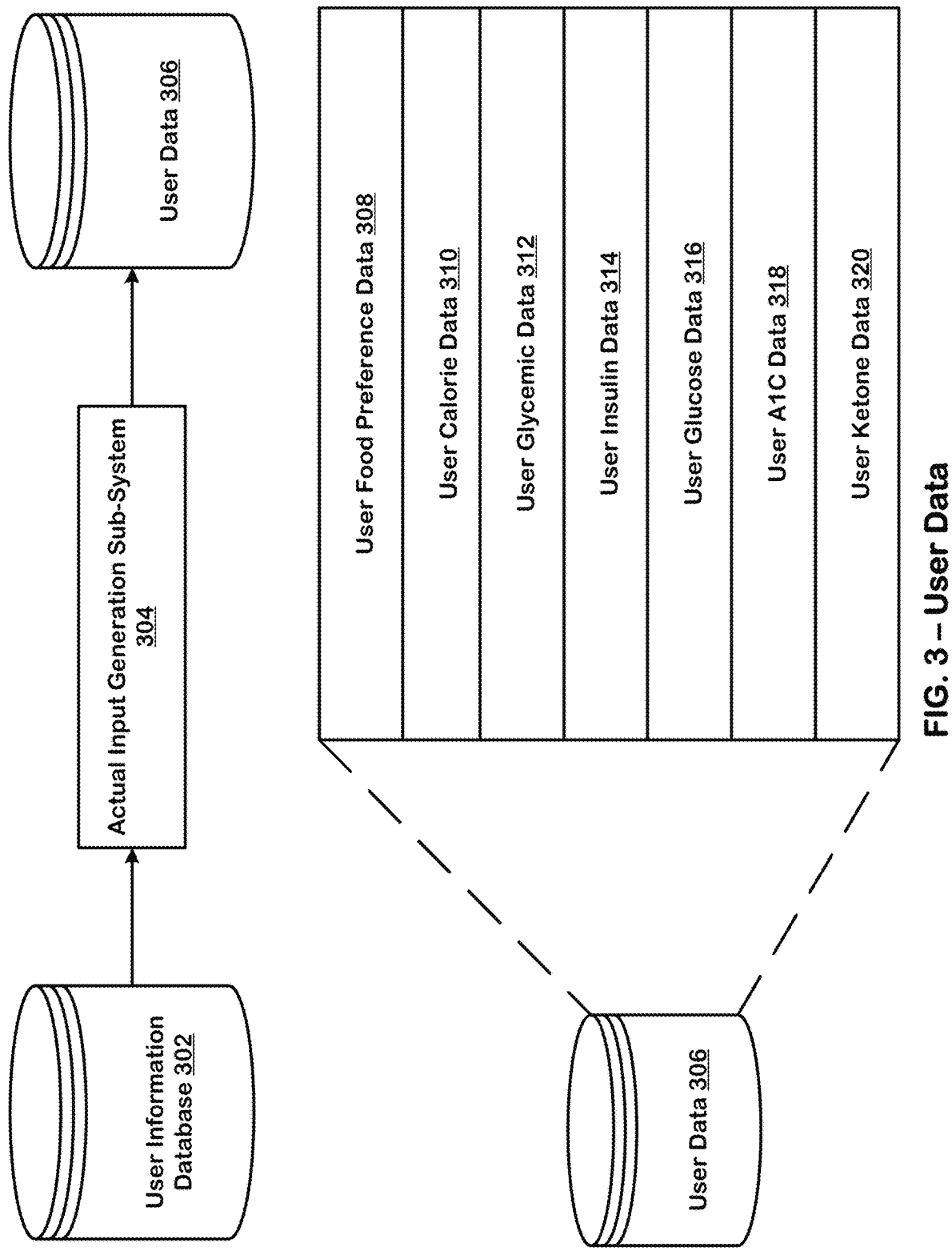
FIG. 3 – User Data

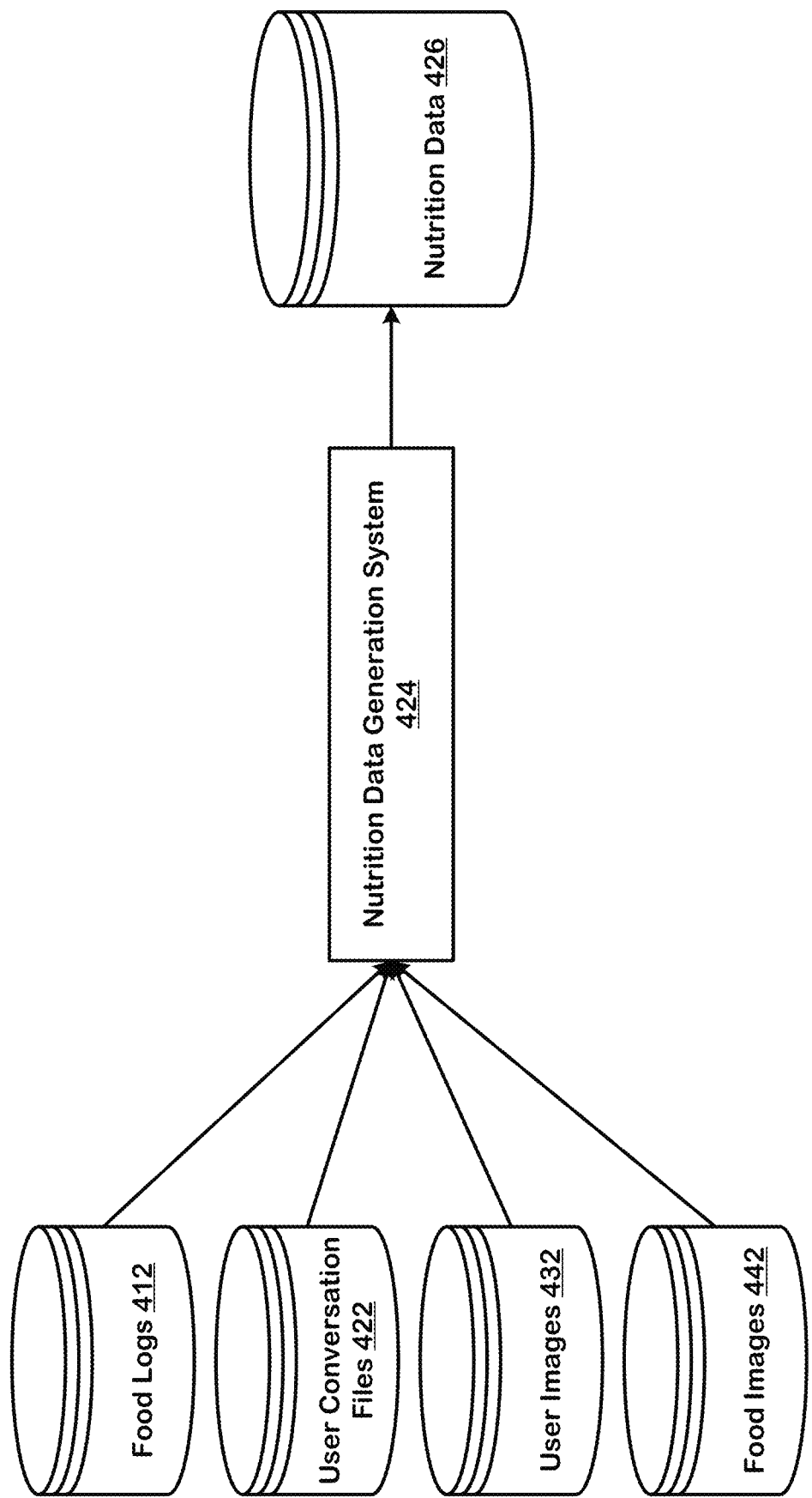
FIG. 4 – Nutrition Data

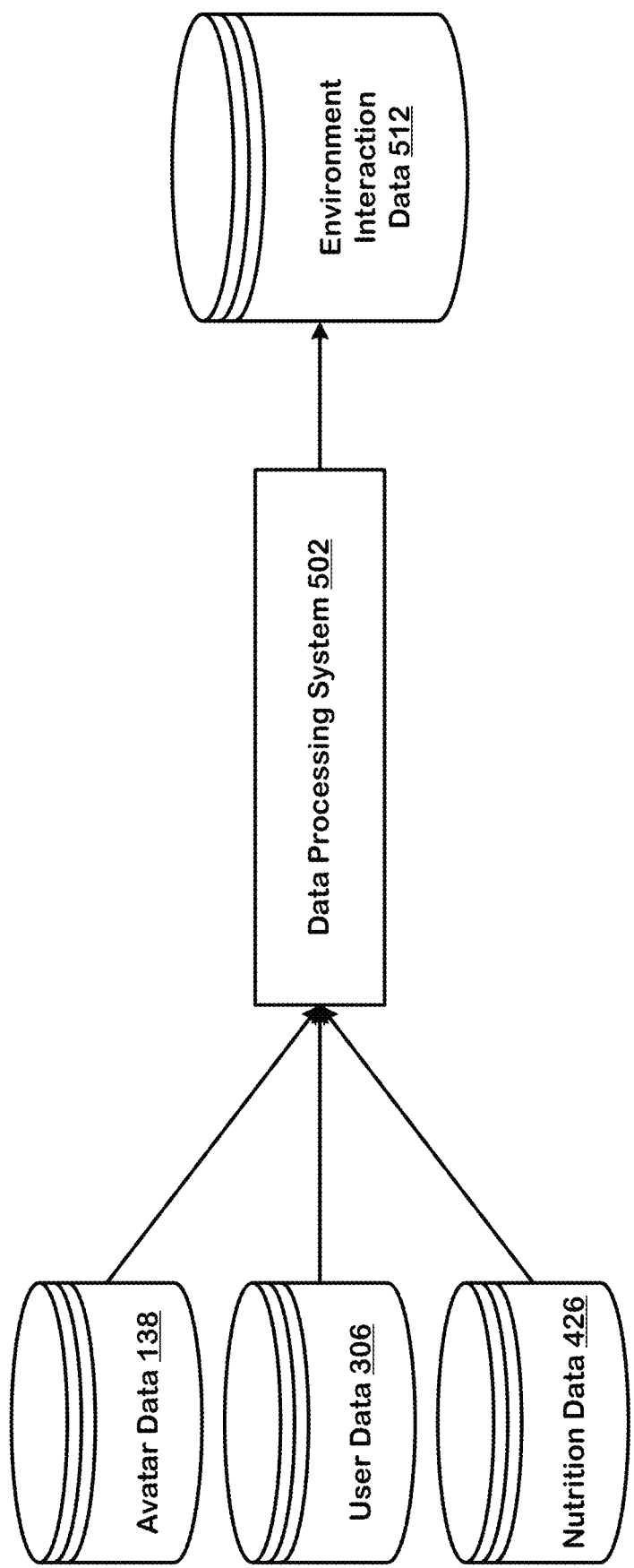
FIG. 5 – Data Processing System

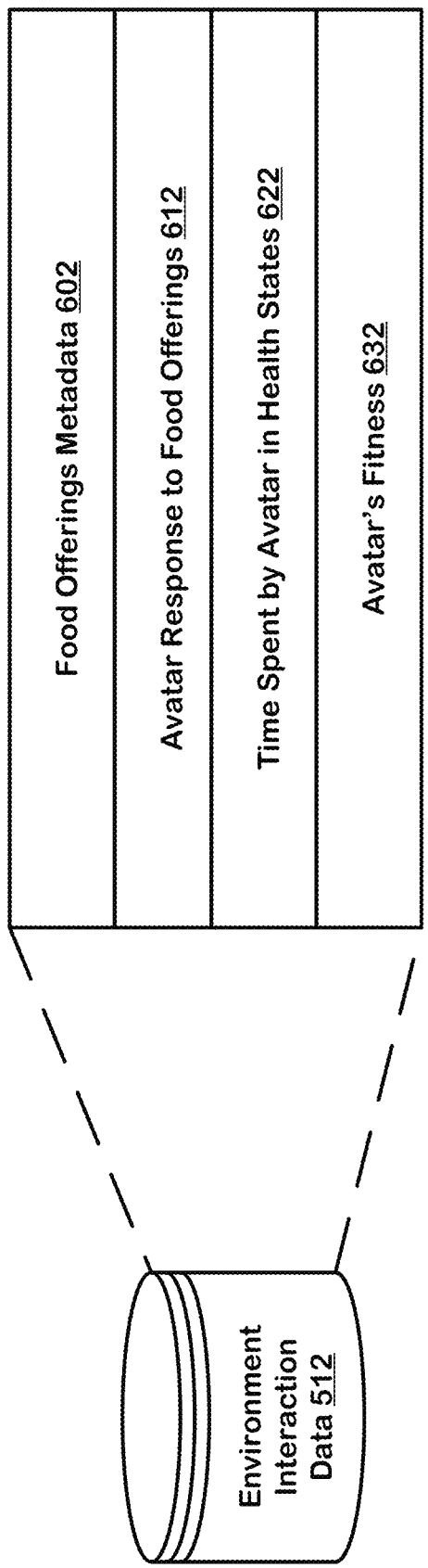
FIG. 6 – Environment Interaction Data

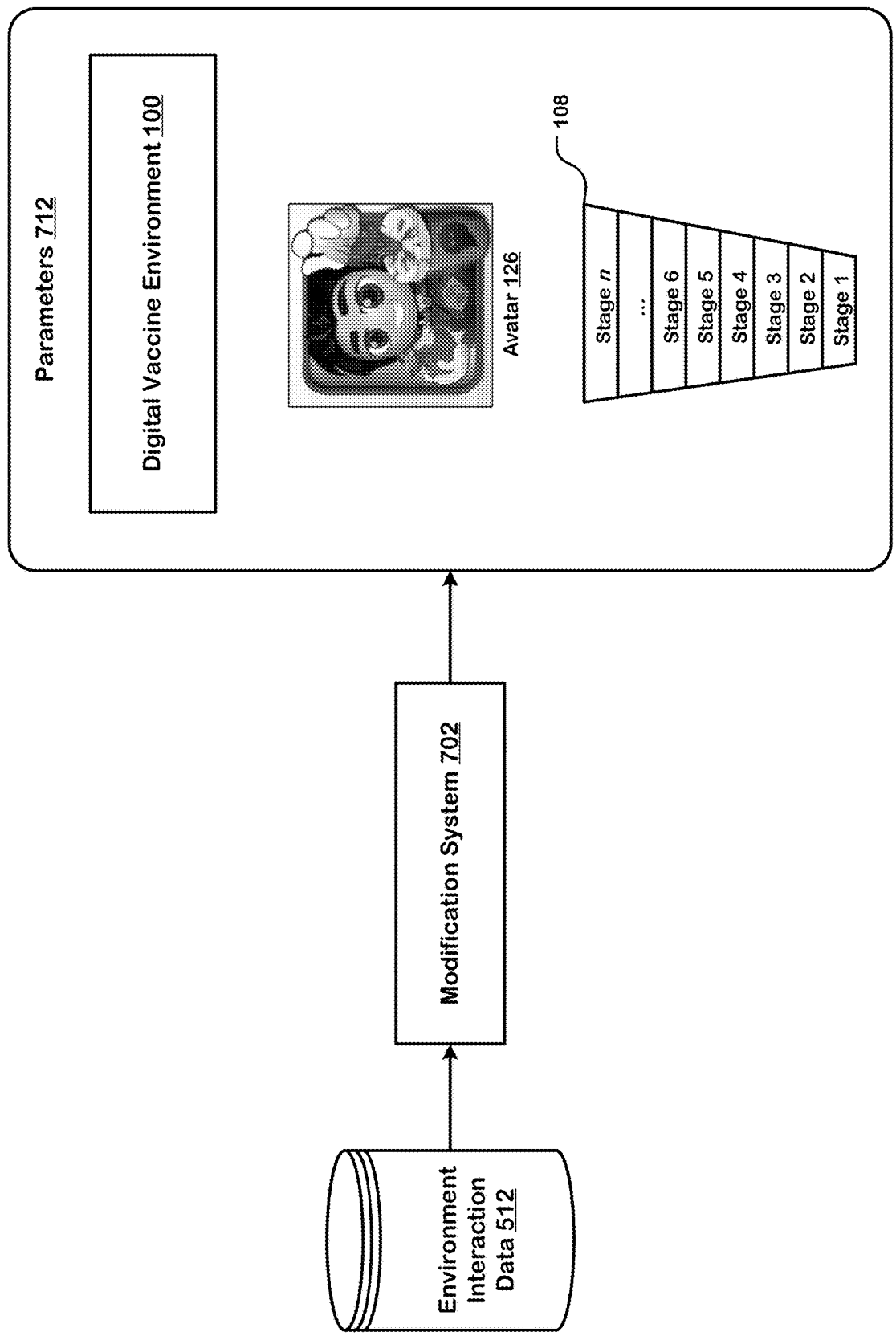
FIG. 7 – Modification System

FIG. 16 – Training

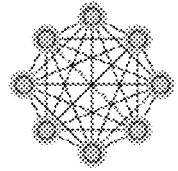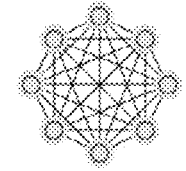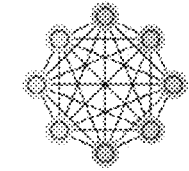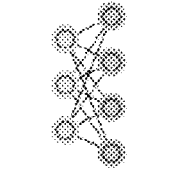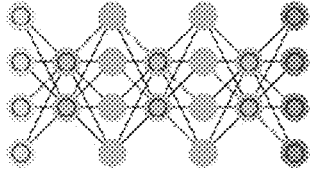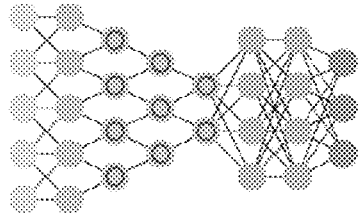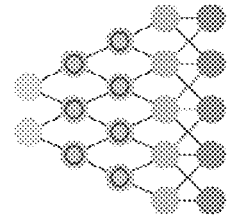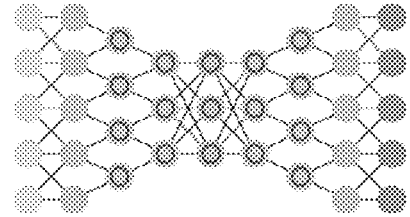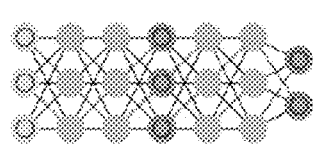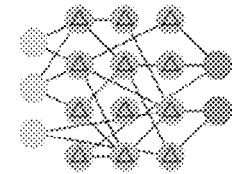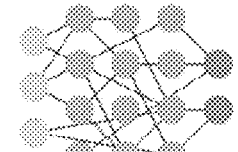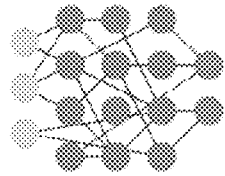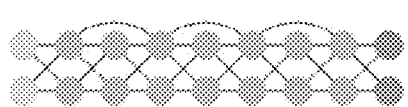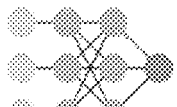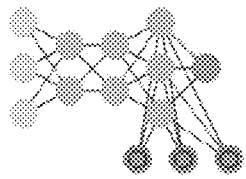
FIG. 17

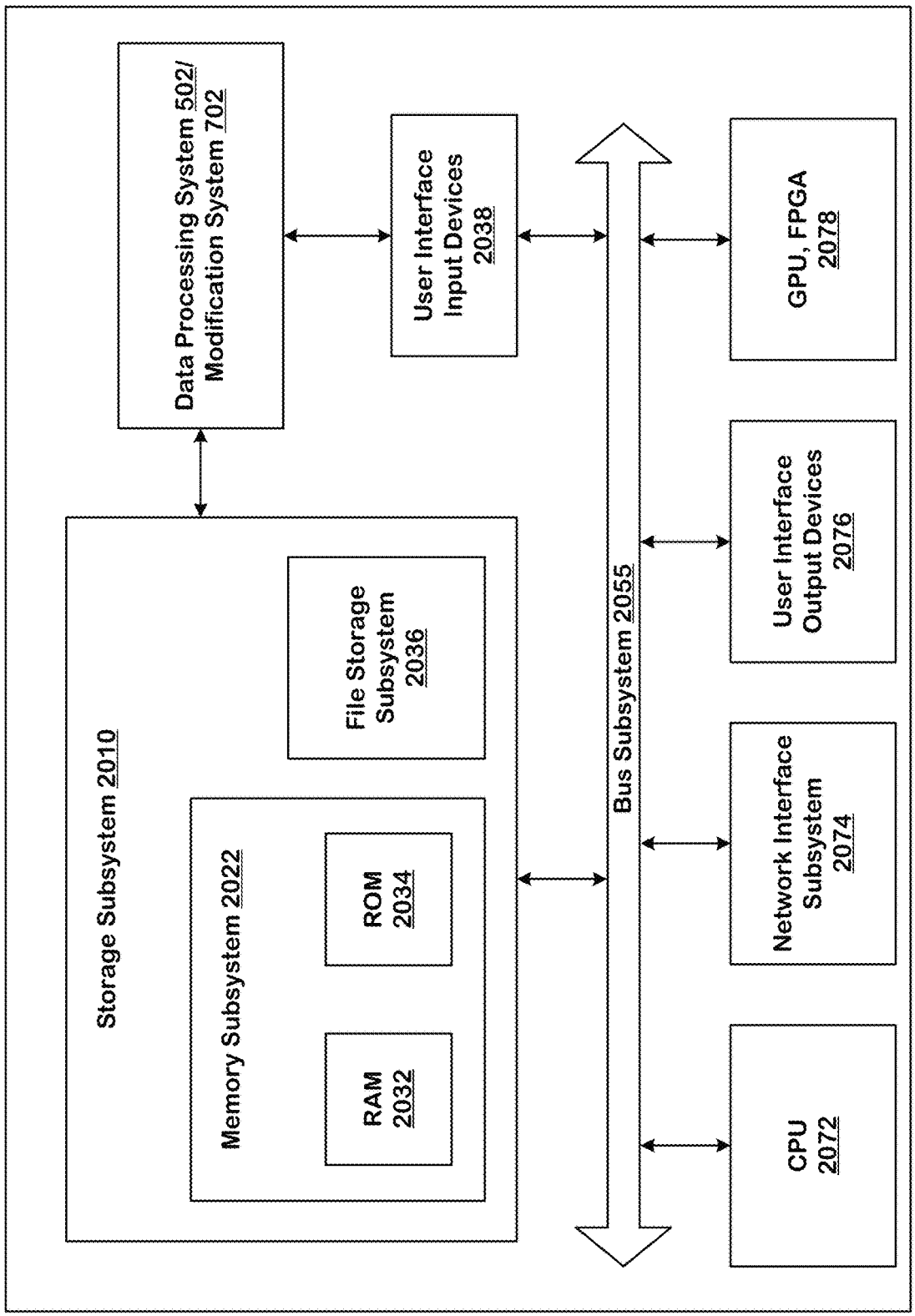
FIG. 20 – Computer System

SYSTEMS AND METHODS FOR DIGITAL VACCINE

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as convolutional neural networks (CNNs) and fully-connected neural networks (FCNNs) for analyzing data.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Machine Learning

In machine learning input variables are used to predict an output variable. The input variables are often called features and are denoted by $X=(X_1, X_2, \ldots, X_k)$, where each $X_i$, $i \in 1, \ldots, k$ is a feature. The output variable is often called the response or dependent variable and is denoted by the variable $Y_i$. The relationship between Y and the corresponding X can be written in a general form:

$$Y = f(X) + \in$$

In the equation above, $f$ is a function of the features ($X_1$, $X_2, \ldots, X_k$) and $\in$ is the random error term. The error term is independent of X and has a mean value of zero.

In practice, the features X are available without having Y or knowing the exact relation between X and Y. Since the error term has a mean value of zero, the goal is to estimate $f$.

$$\hat{Y} = \hat{f} = (X)$$

In the equation above, $\hat{f}$ is the estimate of $\in$, which is often considered a black box, meaning that only the relation between the input and output of $\hat{f}$ is known, but the question why it works remains unanswered.

The function $\hat{f}$ is found using learning. Supervised learning and unsupervised learning are two ways used in machine learning for this task. In supervised learning, labeled data is used for training. By showing the inputs and the corresponding outputs (=labels), the function $\hat{f}$ is optimized such that it approximates the output. In unsupervised learning, the goal is to find a hidden structure from unlabeled data. The algorithm has no measure of accuracy on the input data, which distinguishes it from supervised learning.

Neural Networks

The single layer perceptron (SLP) is the simplest model of a neural network. It comprises one input layer and one activation function. The inputs are passed through the weighted graph. The function $f$ uses the sum of the inputs as argument and compares this with a threshold $\theta$.

A neural network is a system of interconnected artificial neurons (e.g., $a_1$, $a_2$, $a_3$) that exchange messages between each other. The illustrated neural network has three inputs, two neurons in the hidden layer and two neurons in the output layer. The hidden layer has an activation function $f(\bullet)$ and the output layer has an activation function $g(\bullet)$. The connections have numeric weights (e.g., $w_{11}$, $w_{21}$, $w_{12}$, $w_{31}$, $w_{22}$, $w_{32}$, $v_{11}$, $v_{22}$) that are tuned during the training process, so that a properly trained network responds correctly when fed an image to recognize. The input layer processes the raw input, the hidden layer processes the output from the input layer based on the weights of the connections between the input layer and the hidden layer. The output layer takes the output from the hidden layer and processes it based on the weights of the connections between the hidden layer and the output layer. The network includes multiple layers of feature-detecting neurons. Each layer has many neurons that respond to different combinations of inputs from the previous layers. These layers are constructed so that the first layer detects a set of primitive patterns in the input image data, the second layer detects patterns of patterns and the third layer detects patterns of those patterns.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings.

FIG. 1 illustrates one implementation of the technology disclosed operating in a digital vaccine environment.

FIG. 2 shows one example of the avatar data.

FIG. 3 depicts one example of the user data.

FIG. 4 illustrates one implementation of the nutrition data generation system.

FIG. 5 shows one implementation of the data processing system.

FIG. 6 depicts one example of the environment interaction data.

FIG. 7 shows one implementation of the modification system.

FIG. 17 shows different types of neural networks that can be used by the data processing system and the modification system.

FIG. 20 is a simplified block diagram of a computer system that can be used to implement the technology disclosed.

DETAILED DESCRIPTION

Figure 8B:
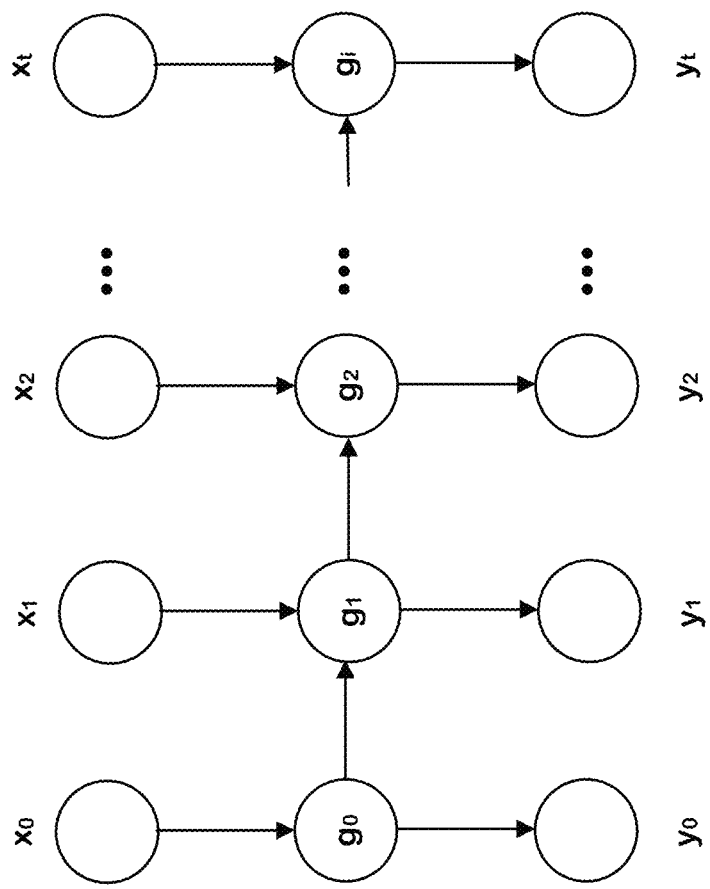
FIGS. 8A and 8B illustrate a recurrent neural network.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

The following description and drawings are illustrative and are not to be construed as limiting. Numerous specific details are described to provide a thorough understanding of the disclosure. However, in certain instances, well-known or conventional details are not described in order to avoid obscuring the description. References to one or an implementation in the present disclosure can be, but not necessarily are, references to the same implementation; and, such references mean at least one of the implementations.

Reference in this specification to "one implementation" or "an implementation" means that a particular feature, structure, or characteristic described in connection with the implementation is included in at least one implementation of the disclosure. The appearances of the phrase "in one implementation" in various places in the specification are not necessarily all referring to the same implementation, nor are separate or alternative implementations mutually exclusive of other implementations. Moreover, various features are described which may be exhibited by some implementations and not by others. Similarly, various requirements are described which may be requirements for some implementations but not other implementations.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various implementations given in this specification.

Without intent to further limit the scope of the disclosure, examples of instruments, apparatus, methods and their related results according to the implementations of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

Implementations of the present disclosure include systems, methods and apparatuses of seamless integration of augmented, alternate, virtual, and/or mixed realities with physical realities for enhancement of web, mobile and/or other digital experiences. Implementations of the present disclosure further include systems, methods and apparatuses to facilitate physical and non-physical interaction/action/reactions between alternate realities.

The disclosed digital vaccine platform enables and facilitates authoring, discovering, and/or interacting with virtual objects (VOBs). One example implementation includes a system and a platform that can facilitate human interaction or engagement with virtual objects (hereinafter, 'VOB,' or 'VOBs') in a digital realm (e.g., an augmented reality environment (AR), an alternate reality environment (AR), a mixed reality environment (MR) or a virtual reality environment (VR)). The human interactions or engagements with VOBs in or via the disclosed environment can be integrated with and bring utility to everyday lives through integration, enhancement or optimization of our digital activities such as web browsing, digital (online, or mobile shopping) shopping, socializing (e.g., social networking, sharing of digital content, maintaining photos, videos, other multimedia content), digital communications (e.g., messaging, emails, SMS, mobile communication channels, etc.), business activities (e.g., document management, document procession), business processes (e.g., IT, HR, security, etc.), transportation, travel, etc.

The disclosed digital vaccine platform provides another dimension to digital activities through integration with the real world environment and real world contexts to enhance utility, usability, relevancy, entertainment and/or vanity value through optimized contextual, social, spatial, temporal awareness and relevancy. In general, the virtual objects depicted via the disclosed system and platform can be contextually (e.g., temporally, spatially, socially, user-specific, etc.) relevant and/or contextually aware. Specifically, the virtual objects can have attributes that are associated with or relevant to real world places, real world events, humans, real world entities, real world things, real world objects, real world concepts and/or times of the physical world, and thus its deployment as an augmentation of a digital experience provides additional real life utility.

Note that in some instances, VOBs can be geographically, spatially and/or socially relevant and/or further possess real life utility. In accordance with implementations of the present disclosure, VOBs can be or appear to be random in appearance or representation with little to no real world relation and have little to marginal utility in the real world. It is possible that the same VOB can appear random or of little use to one human user while being relevant in one or more ways to another user in the AR environment or platform.

The disclosed digital vaccine platform enables users to interact with VOBs and deployed environments using any device, including by way of example, computers, PDAs, phones, mobile phones, tablets, head mounted devices, goggles, smart watches, monocles, smart lens, smart watches and other smart apparel (e.g., smart shoes, smart clothing), and any other smart devices.

In one implementation, the disclosed digital vaccine platform is analogous to, or operates in conjunction with the Web for the physical world. The host server can provide a browser, a hosted server, and a search engine, for this new Web.

Implementations of the disclosed digital vaccine platform enables content (e.g., VOBs, third party applications, AR-enabled applications, or other objects) to be created and placed into layers (e.g., components of the virtual world, namespaces, virtual world components, digital namespaces, etc.) that overlay dietary information by anyone, and focused around a layer that has the highest number of audience (e.g., a public layer). The public layer can in some instances, be the main discovery mechanism and source for advertising venue for monetizing the disclosed platform.

In one implementation, the disclosed digital vaccine platform includes a virtual world that exists in another dimension superimposed on the physical world. Users can perceive, observe, access, engage with or otherwise interact with this virtual world via a user interface of client application.

One implementation of the disclosed digital vaccine platform includes a consumer or client application component (e.g., as deployed on user devices) which is able to provide dietary awareness to human users of the AR environment and platform. The client application can sense, detect or recognize virtual objects and/or other human users, actors, non-player characters or any other human or computer participants that are within range of their physical location, and can enable the users to observe, view, act, interact, react with respect to the VOBs.

Furthermore, implementations of the disclosed digital vaccine platform also include an enterprise application (which can be desktop, mobile or browser based application). In this case, retailers, advertisers, merchants or third-party e-commerce platforms/sites/providers can access the disclosed platform through the enterprise application which enables management of paid advertising campaigns deployed via the platform.

Users can access the client application which connects to the host platform (e.g., as hosted by a host server). The client application enables users to sense and interact with virtual objects ("VOBs") and other users ("Users"), actors, non-player characters, players, or other participants of the platform. The VOBs can be marked or tagged (by QR code, other bar codes, or image markers) for detection by the client application.

The client devices can be any system and/or device, and/or any combination of devices/systems that is able to establish a connection with another device, a server and/or other systems. Client devices each typically include a display and/or other output functionalities to present information and data exchanged between among the devices and the host server.

For example, the client devices can include mobile, hand held or portable devices or non-portable devices and can be any of, but not limited to, a server desktop, a desktop computer, a computer cluster, or portable devices including, a notebook, a laptop computer, a handheld computer, a palmtop computer, a mobile phone, a cell phone, a smart phone, a PDA, a Blackberry device, a Treo, a handheld tablet (e.g. an iPad, a Galaxy, Xoom Tablet, etc.), a tablet PC, a thin-client, a hand held console, a hand held gaming device or console, an iPhone, a wearable device, a head mounted device, a smart watch, a goggle, a smart glasses, a smart contact lens, and/or any other portable, mobile, hand held devices, etc. The input mechanism on client devices can include touch screen keypad (including single touch, multi-touch, gesture sensing in 2D or 3D, etc.), a physical keypad, a mouse, a pointer, a track pad, motion detector (e.g., including 1-axis, 2-axis, 3-axis accelerometer, etc.), a light sensor, capacitance sensor, resistance sensor, temperature sensor, proximity sensor, a piezoelectric device, device orientation detector (e.g., electronic compass, tilt sensor, rotation sensor, gyroscope, accelerometer), eye tracking, eye detection, pupil tracking/detection, or a combination of the above.

The client devices, application publisher/developer, its respective networks of users, a third-party content provider, and/or promotional content server, can be coupled to the network and/or multiple networks. In some implementations, the client devices and host server may be directly connected to one another. The alternate, augmented provided or developed by the application publisher/developer can include any digital, online, web-based and/or mobile based environments including enterprise applications, entertainment platforms, gaming platforms, social networking platforms, e-commerce, exchanges, search platforms, browsing, discovery, messaging, chatting, and/or any other types of activities (e.g., network-enabled activities).

Motivation

Artificial Intelligence (AI) holds vast potential in reshaping the human condition.

Entire industries are poised for being rescripted at their core. Much of AI has been oriented towards replacing human tasks. Image recognition, Natural Language Processing, news feed/digital content curation and click-through optimization, represent narrow use cases of AI in enhancing advertising-driven business models of digital content platforms. AI is now making headway, as human decision making can be replaced, by better informed algorithms at greater speed. Driverless cars, robotics, drones, transportation, manufacturing, etc represent another exciting facet of application of AI, especially as it can minimize human error, within the context of improving efficiency within pre-existing industries. Neural networks represent one of the most powerful elements of AI, as outcomes can begin to mirror biological intelligence that can learn to adapt based on experience, powered by data. Such advances could conceivably culminate in human vs AI conflict, especially in cases when AI-enabled precision outcomes, become pawns of rogue intent. While most of the focus and directionality for AI have been towards automation of existing processes through data mining and machine learning, the AI revolution holds promise for inverting the paradigm, with respect to several planetary-scale crises. There is an exciting role for AI, to empower human beings in unprecedented ways. Human intelligence and consciousness can be elevated through a more capable and well-intentioned greater force. The creation of such AI would call for a tremendous sense of purpose and deeper extents of ethical innovation by the designers of such AI-enabled augmentation.

This invention is meant to fulfill a vision to eradicate the preventable nutrition and lifestyle related global burden of diabetes, cardiovascular disease, hypertension, kidney disease, liver disease, cognitive disease and cancer, as well as find relevance in reducing symptoms of illness, through our platform of DV+AI.

The past decade has been dedicated towards a high standard of self-funded science and innovation, bound by ethical review and the scientific process of evidence-based iterative inquiry, towards a mission to develop AI that can empower humans for generations to come. The fundamental realization has been that humans are already attacking our own, as unbridled profit motive turns a blind eye to human-planetary cost. The fundamental global trend that must be opposed, is that there is vast profit captured by few, from the treatment, diagnosis, and perpetuation of human sickness globally. Enormous profit is captured through capitalism fueled efficiency, increasingly AI-powered algorithmic assault, upon human health at the individual and societal level. The long list of symptomatic evidence of this tragic reality ranges from the proliferation of conglomerate fueled processed food, which feeds the other end of the spectrum— the colossal force of modern medicine and big pharmaceutical companies. Both these domineering industries profit from undermining human potential.

It is an open secret that modern medicine has reached vulgar levels of ethical and moral conflict, as doctors in corporate PE controlled hospitals, make commissions and are manipulated to meet incentivized "sales quotas" on one hand, while they dishonorably prescribe more invasively debilitating medications that cause more harm than the diseases they claim to treat. "Do no harm" is simply not reconcilable when there is increasingly more money at stake from over-diagnosing, over-treating, creating more long-lasting dependency, which is ultimately killing people. The Insulin crisis, the opioid crisis, the cholesterol sham, the chemotherapy scam, thyroid treatment, increasing C-sections, PE fueled price gouging, are just the proverbial tip of the iceberg, representing the extent and scale of injustice against humanity. It is way overdue that we restore the human condition to levels of natural equilibrium embodied in ancient cultures and traditions, which were designed at a time when wealth did not conflict with human health. One such familiar source of inspiration for our team is the Ayurveda, which is built upon a foundational commitment to "Swasthasya swasthya rakshanam. Aturasya roga nivaranam" (To protect health. To prevent disease—Charaka Samhita 500 B.C). One can contrast such a gentle biologically aligned philosophy to our modern-day reality, where dubious treatments backed by ulterior profit motives, become veiled behind the Hippocratic Oath (Do no harm) to capitalize on biologically violent, protocol-driven treatments, which are validated via an irreproducible reductionist lens of evidence.

Digital vaccine (DV) plus (+) artificial intelligence (AI) exists to rescript this global trend, at scale, with a solemn aim to empower humanity by protecting our health and enhancing human potential by reducing health risk. This synthesis of technology is designed to attain this goal, while living up to sublime standards that can reorient capitalism, in favor of protecting health, rather than treating sickness. Our methods of DV are built upon fundamental neuroscience breakthroughs in Neuromodulation and neurostimulation, at the mechanistic and physiological level, through non-invasive technology. This allows development of deep technology and fundamental know-how.

The investment thesis in favor of DV+AI is quite simple. The rough estimate of the aggregate of the global market cap of pharmaceutical companies, hospital systems and healthcare delivery spend, amounts to more than $15 Trillion. The economic burden of global healthcare annual spend is a staggering $20+ Trillion. The vast burden of disease has shifted, while continuing to shift, towards profit fueled preventable Non Communicable Diseases (NCDs). The even more macabre forecast is that these numbers are projected to grow with unforeseen acceleration. Through highly scalable DV+AI, a small fraction of the economic value created can be captured, as DV+AI will disintermediate the current capitalistic machinery that profits from sickness. Given the early stages of the field being defined and the commercialization traction through a current SaaS-like monthly subscription model (distributing to each student via mobile devices) a mandatory health education co-curriculum and co-scholastic program is being shaped, as a result of distribution through qualified distinguished school partners of the DV project. DV+AI is already getting to the market by filling a void for clinically proven science-based nutrition-health education curriculum. Given that DV+AI is a subset of DTx, this is particularly significant given the current state of confusion about viable go to market models among contemporary adjacent DTx companies, many of whom have raised several 100s of millions of dollars, to tackle much smaller scope of disease through non-scalable technology. As continuing focus on population health grows DV+AI will attain levels of evidence that becomes irrefutable from a reimbursement perspective. Based on our time tested partnerships with world leading researchers at academic research institutions, like Carnegie Mellon University, Stanford School of Medicine, Stanford Law School, Johns Hopkins University Bloomberg School of Public Health, Pittsburgh Children's Hospital of UPMC, Oxford University Nuffield Department of Medicine, Baylor College of Medicine, National University of Singapore and the like, we aim to define the category and calibration standards of DV+AI. We are already preparing for randomized controlled clinical trials, through our pre-existing and expanding network of renowned life science researchers, with a clear scientific aim to measure outcomes of DV+AI on cholesterol (HDL/LDL), blood glucose, A1c, Ketones, Glycoprotein Acetyls, Amino acids, Body mass Index BMI, Cognitive development markers. DV+AI is therefore squarely in the turf of pharmaceutical and biotech companies. DV+AI presents the world a non-invasive, relatively risk-free and rigorous science-based alternative, to invasive medications and treatments, with a foundation of science will set a high bar for future competitors, by building a moat based on medical-grade published longitudinal outcomes. Through partnerships, we will continue to push to set a global standard for a compulsory DV for every child in our world, backed by recommendations and policy frameworks from ministries of health/education. DV+AI is also on the cusp of gaining endorsement from organizations such as World Health Organization (WHO)/United Nationa Children's Fund (UNICEF)/United Nations Development Program (UNDP). This focus on science will keep go-to-market marketing costs low while leveraging the groundbreaking science with world-renowned academic partners. This unique synthesis of highly scalable software based innovation, which can be protected through an IP estate, will ensure software levels of profitability.

An audacious goal is to create a company with a multi-century horizon that surpasses market value in excess of $1 Trillion, driven by uncompromising mission to garner the requisite influence and resources, to rescript the future of human potential. This mission is always relevant because of a belief that good health will always be crucial for true happiness and therefore, will remain the greatest wealth to be passed on to future generations.

Digital Vaccine Environment

We describe a system and various implementations for providing a digital vaccine solution. The system and processes are described with reference to FIG. 1. Because FIG.

1 is an architectural diagram, certain details are intentionally omitted to improve the clarity of the description. The discussion of FIG. 1 is organized as follows. First, the elements of the figure are described, followed by their interconnections. Then, the use of the elements is described in greater detail.

FIG. 1 illustrates one implementation of the technology disclosed operating in a digital vaccine environment 100. User 102 uses devices such as smartphones, tablets, laptops, and personal computers (PCs) to interface with the digital vaccine environment 100. The digital vaccine environment 100 is responsive to user input 112 provided by the user 102.

The digital vaccine environment 100 can be run by a game processor like physics engine 140, which implements the digital vaccine environment 100 in a gamified context centered at an avatar 126. The physics engine 140 can be UNITY 3D™ or HAVOK™. The physics engine 140 can be configured with logic that specifies the narrative, stages, tasks, animations, and simulations of the digital vaccine environment 100 that the avatar 126 goes through and interacts with, including rules that govern how the avatar 126 is modified as it operates within the digital vaccine environment 100 based on the user input 112.

The digital vaccine environment 100 further comprises an avatar appearance engine 106, a virtual input generation sub-system 136, a performance database 114, a tasks database 118, a food offerings database 128, and an avatar data database 138.

The modules of the digital vaccine environment 100 can be implemented in hardware or software, and need not be divided up in precisely the same blocks as shown in FIG. 1. Some of the modules can also be implemented on different processors or computers, or spread among a number of different processors or computers. In addition, it will be appreciated that some of the modules can be combined, operated in parallel or in a different sequence than that shown in FIG. 1 without affecting the functions achieved. Also as used herein, the term "module" can include "sub-modules," which themselves can be considered to constitute modules. The blocks in the digital vaccine environment 100, designated as modules, can also be thought of as flowchart steps in a method. A module also need not necessarily have all its code disposed contiguously in memory; some parts of the code can be separated from other parts of the code with code from other modules or other functions disposed in between.

The interconnections of the elements of the digital vaccine environment 100 are now described. The actual communication path can be point-to-point over public and/or private networks. Some items might be delivered indirectly, e.g., via an application store (not shown). The communications can occur over a variety of networks, e.g., private networks, VPN, MPLS circuit, or Internet, and can use appropriate application programming interfaces (APIs) and data interchange formats, e.g., Representational State Transfer (REST), JavaScript Object Notation (JSON), Extensible Markup Language (XML), Simple Object Access Protocol (SOAP), Java Message Service (JMS), and/or Java Platform Module System. All of the communications can be encrypted. The communication is generally over a network such as the LAN (local area network), WAN (wide area network), telephone network (Public Switched Telephone Network (PSTN), Session Initiation Protocol (SIP), wireless network, point-to-point network, star network, token ring network, hub network, Internet, inclusive of the mobile Internet, via protocols such as EDGE, 3G, 4G LTE, Wi-Fi, and WiMAX. Additionally, a variety of authorization and authentication techniques, such as username/password, Open Authorization (OAuth), Kerberos, SecureID, digital certificates, voice recognition, fingerprint scan, facial recognition, biometric scanc and more, can be used to secure the communications.

The digital vaccine environment 100 can be accessed via an application programming interface (API). An API refers to a packaged collection of code libraries, routines, protocols methods, and fields that belong to a set of classes, including its interface types. The API defines the way that developers and programmers can use the classes for their own software development, just by importing the relevant classes and writing statements that instantiate the classes and call their methods and fields. An API is a source code-based application intended to be used as an interface by software components to communicate with each other. An API can include applications for routines, data structures, object classes, and variables. Basically, an API provides an interface for developers and programmers to access the underlying data, platform capabilities, and features of cloud-based services. Implementations of the technology disclosed use different types of APIs, including web service APIs such as HTTP or HTTPs based APIs like SOAP, WSDL, Bulk, XML-RPC and JSON-RPC and REST APIs (e.g., FLICKR™, GOOGLE STATIC MAPS™, GOOGLE GEOLOCATION™), web socket APIs, library-based APIs like JavaScript and TWAIN (e.g., GOOGLE MAPS™ JavaScript API, DROPBOX™ JavaScript Data store API, TWILIO™ APIs, Oracle Call Interface (OCI)), class-based APIs like Java API and Android API (e.g., GOOGLE MAPS™ Android API, MSDN Class Library for .NET Framework, TWILIO™ APIs for Java and C #), OS functions and routines like access to file system and access to user interface, object remoting APIs like CORBA and .NET Remoting, and hardware APIs like video acceleration, hard disk drives, and PCI buses. Other examples of APIs used by the technology disclosed include AMAZON EC2 API™, BOX CONTENT API™, BOX EVENTS API™, MICROSOFT GRAPH™, DROPBOX API™, DROPBOX API v2™, DROPBOX CORE API™, DROPBOX CORE API v2™, FACEBOOK GRAPH API™, FOURSQUARE API™, GEONAMES API™, FORCE.COM API™, FORCE.COM METADATA API™, APEX API™, VISUALFORCE API™, FORCE.COM ENTERPRISE WSDL™, SALESFORCE.COM STREAMING API™, SALESFORCE.COM TOOLING API™, GOOGLE DRIVE API™, DRIVE REST API™, ACCUWEATHER API™, and aggregated-single API like CLOUDRAIL™ API.

Having introduced the elements of FIG. 1 and their interconnections, elements of the figure are now described in greater detail.

The digital vaccine environment 100 presents the user-driven avatar 126 with (i) tasks 118 that test the avatar's physical fitness and (ii) food offerings 128 at various stages 108 of the play (game). The appearance of the avatar 126 is responsive to the avatar's performance 114 on the tasks 118 and selection of the food offerings 128. For example, the avatar 126 is offered increasingly difficult physical exertion challenges as it progresses through the various stages 108 of the play (game). As the avatar 126 successfully performs the physical tasks, its appearance becomes healthier and fitter (e.g., muscular, thinner). In another example, the avatar 126 is offered a variety of food types with different nutritional values and calorie counts. Based on the food consumed, the appearance of the avatar 126 changes (e.g., less muscular, bulkier). In one implementation, the changes in the appearance of the avatar 126 are implemented by the avatar appearance engine 106. Also, the movement and activity of the avatar 126 is controlled by the user input 112.

An input generation system has a virtual input generation sub-system 136 and an actual input generation sub-system 304. The virtual input generation sub-system 136 monitors the avatar's progression through the digital vaccine environment 100 and produces avatar data 138.

FIG. 2 illustrates one example of the avatar data 138. In one implementation, the avatar data 138 includes (i) avatar food preference data 202, (ii) avatar calorie data 212, (iii) avatar insulin data 222, (iv) avatar glucose data 232, (v) avatar A1C data 242, and (vi) avatar ketone data 252 (vii) avatar cholesterol (HDL/LDL) data (viii) avatar amino acids data (ix) avatar glycoprotein acetyls data (x) avatar gut microbiome data.

The avatar food preference data 202 further comprises time stamped virtual food presented to the avatar in the digital vaccine environment, and time stamped virtual food selected by the avatar in the digital vaccine environment. The avatar calorie data 212 further comprises total calorie level of the avatar, calories expanded by the avatar as a result of performing the tasks, and net calorie level of the avatar. The avatar insulin data 222 further comprises virtual insulin dose counter, and virtual insulin units. The avatar glucose data 232 further comprises virtual net blood glucose. The avatar A1C data 242 further comprises virtual A1C results. The avatar ketone data 252 further comprises virtual ketone level.

FIG. 3 illustrates one example of the user data 306. The actual input generation sub-system 304 accesses a user information database 302 and produces the user data 306. In one implementation, the user data 306 includes (i) user food preference data 308, (ii) user calorie data 310, (iii) user glycemic data 312, (iv) user insulin data 314, (v) user glucose data 316, (vi) user A1C data 318, and (vii) user ketone data 320 (vii) user cholesterol (HDL/LDL) data (viii) user amino acids data (ix) user glycoprotein acetyls data (x) user gut microbiome data (FIG. 3 must be modified to include these indicators).

In some implementations, the actual input generation sub-system 304 is a web crawler that collects the user data 306 from online biographic sources such as social media sites, clinician input or Electronic Health Records.

The user food preference data 308 further comprises time stamped actual food presented to the user in real world, and time stamped actual food consumed by the user in the real world. The user calorie data 310 further comprises actual calories consumed by the user in the real world, and calories expanded by the user in the real world. The user glycemic data 312 further comprises glycemic index, and glycemic load. The user insulin data 314 further comprises actual insulin dose counter, and actual insulin units. The user glucose data 316 further comprises actual net blood glucose. The user A1C data 318 further comprises actual A1C results. The user ketone data 320 further comprises actual ketone level. The user HDL/LDL data further comprises the actual cholesterol data. The user amino acids data further comprises actual amino acid level. The user glycoprotein acetyls data further comprises the actual glucoprotein acetyls level. The user gut microbiome data further comprises the actual gut microbiome data.

FIG. 4 illustrates one implementation of the nutrition data generation system 424. The nutrition data generation system 424 processes (i) food logs 412, (ii) user conversation files 422, (iii) user images 432, and/or (iv) food images 442 and produces nutrition data 426.

The nutrition data generation system 424 can use deep neural networks. Deep neural networks are a type of artificial neural networks that use multiple nonlinear and complex transforming layers to successively model high-level features. Deep neural networks provide feedback via back-propagation which carries the difference between observed and predicted output to adjust parameters.

Deep neural networks are a family of parametric, non-linear and hierarchical learning functions. Given a dataset D, deep neural networks need to find the optimal parameters θ that minimize some loss function. These models are called networks because they are a collection of functions that can be represented as an acyclic graph. The acyclic graph is divided into layers, and each layer represents a computation of the form:

$$h_1 = f_1(W_1 \cdot x + b_1)$$

where x is the multidimensional input of the model that is mapped to the hidden unit $h_1$ using weights $W_1 \in \theta$ and biases $b_1 \in \theta$. The function f1(•) is called an activation function. The output of one layer can be used as input for another layer.

$$h_2 = f_2(W_2 \cdot f_1(W_1 \cdot x + b_1) + b_2)$$

Hence the hierarchical aspect of neural networks. The field of deep learning focuses on neural networks with a large number of these layers because they are capable of approximating more complex functions.

In one implementation, the nutrition data generation system 424 is a recurrent neural network that processes the user conversation files 422 and produces the nutrition data 426. Recurrent neural networks (RNN) are part of the family of deep neural networks and are able to process sequential data. To understand the information that is incorporated in a sequence, an RNN needs memory to know the context of the data. Information about the past is passed through the network using hidden states. Therefore a single computational unit can be dependent on its previous states. The idea of using RNN's is to get a natural way of the persistence of memory. The cycles allow the RNN's to get this persistence behavior. FIG. 8A illustrates a schematic representation of an RNN, where g is a part of a neural network and should not be confused with the activation function.

Figure 8A:
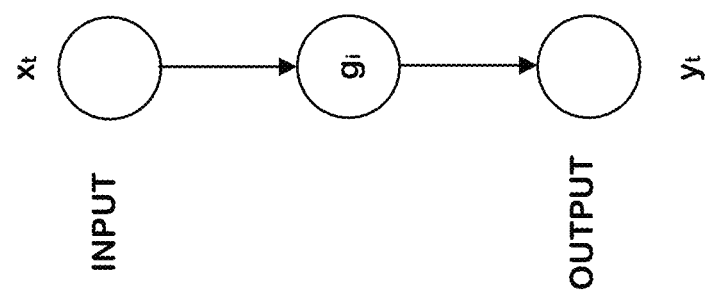

The unfolded network in FIG. 8B clarifies how an RNN works. It can be seen as a neural network composed of smaller neural networks in which information is passed in an ordered way. The unfolded network shows that if t represents the time, causality relations hold in these type of networks. This makes the RNN interesting for studying time series. In the study of time series on a daily basis, seasonal features need to be detected. The period of a season can become relatively large. Theoretically, it should be possible to learn any relation between the past with the current time, since the information is passed through each block. However, learning long term dependencies for RNN's using gradient descent algorithms is difficult.

Figure 9:
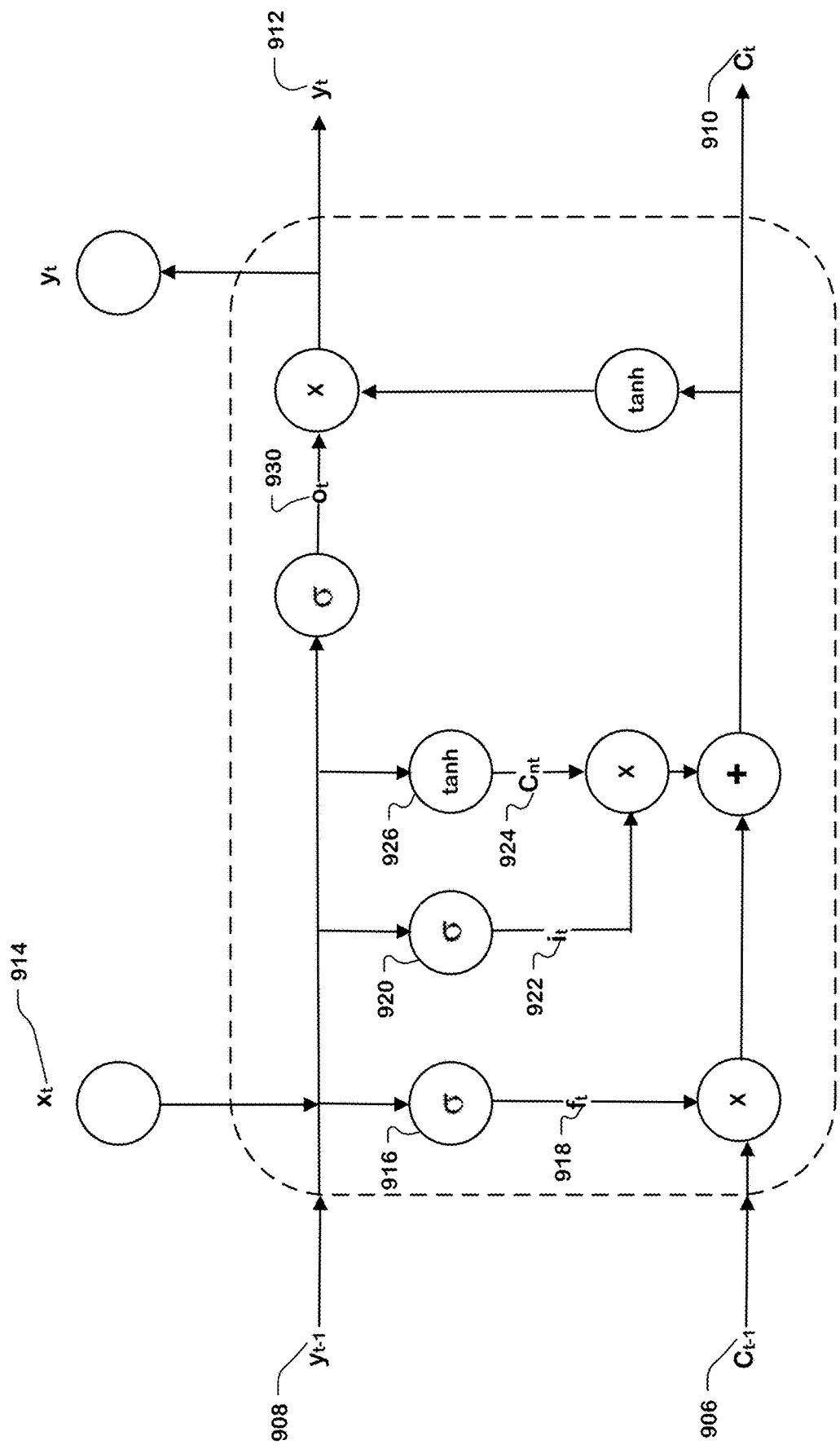
FIG. 9 illustrates an example LSTM block.

The Long Short Term Memory (LSTM) recurrent neural network is designed to be able to learn these long-term relations without overlooking the short-term dependencies. FIG. 9 illustrates a block of an LSTM. In FIG. 9, × and + are point-wise operators, and σ and tan h are activation functions. Two joining arrows make a concatenate operation. Two splitting arrows make a copy operation. The LSTM block is repeated in the same way as the RNN. The LSTM block consists of two lines passing horizontally, the y-value which corresponds to the output of a block and the C-value which corresponds to the cell state. The horizontal lines have inputs $C_{t-1}$ 906 and $y_{t-1}$ 908 from the preceding blocks, and outputs $C_t$ 910 and $y_t$ 912 to the succeeding blocks. Vertically, for each block, there is an input x and an output y.

Starting with the input $x_t$ 914, the signal is concatenated with $y_{t-1}$ 908 to obtain $[y_{t-1}, x_t]$. Following the first arrow pointing downwards, the values are passed through a sigmoid function σ 916. The output $f_t$ 918 of the sigmoid function σ 916 function is defined as:

$$f_t = \sigma(W_f \cdot [y_{t-1}, x_t] + b_f)$$

The function above is called the forget gate, since the output, a value in (0, 1), decides whether the preceding cell state is remembered or forgotten using the point-wise product operator.

Following the second arrow pointing downwards, the signal $[y_{t-1}, x_t]$ arrives at another sigmoid function σ 920 which is called the input gate. The output $i_t$ 922 decides which values are used for the update. The output $i_t$ 922 is:

$$i_t = \sigma(W_i \cdot [y_{t-1}, x_t] + b_i)$$

The third arrow pointing downwards generates new candidate values $C_{nt}$ 924 for the cell state by using the tan h function 926. By taking the cross product with the input gate, the update for the cell state can be determined using:

$$C_{nt} = \tan h(W_C \cdot [y_{t-1}, x_t] + b_C)$$

$$C_t = f_t * C_{t-1} + i_t * C_{nt}$$

The new cell state is a combination of the old cell state and the new candidate in which the forget gate and the input gate gradual decide whether to use the old cell state and new input respectively.

The output gate $o_t$ 930 transforms the signal $[y_{t-1}, x_t]$ as defined by:

$$o_t = \sigma(W_o \cdot [y_{t-1}, x_t] + b_o)$$

By taking the product of the tan h of the updated cell state Ct 910 and the output gate $o_t$ 930, the new output $y_t$ 912 is defined as:

$$y_t = o_t * \tan h(C_t)$$

The main components of the LSTM are the cell state and the output. The new cell state is defined by the forget gate and input gate. The new output is defined by the output gate and the new cell state. By adding n of these blocks, the size of the vectors passing through the blocks is growing linearly.

In other implementations, the nutrition data generation system 424 can be an XGBoosted tree or a decision tree.

XGBoost stands for eXtreme Gradient Boosting, and it is a distributed implementation of gradient boosting with emphasis on efficiency, flexibility, and portability. It provides parallel tree boosting and is faster when compared with other gradient boosting implementation.

A decision tree is a model that begins with a single non-leaf node that branches into different outcomes. Then the outcomes lead to more additional nodes. Each non-leaf node represents the test on one particular feature, each branch represents the outcome of this feature, and each leaf node stores a classification. Once the split for each feature is done, the one with the minimum loss is viewed as the best split criteria and set it as a rule for that node. The splitting process keeps going until the termination condition is met.

Boosting technique holds the principle that a combination of weak classifiers can create a single strong classifier. Weak classifiers are classifiers that tend to perform insufficiently when applied in isolation but well when combined with other weak classifiers trained on the same dataset. For the boosting methods, the additive training method is applied in each step, during which a week classifier is added to the model. In XGBoost, the weak classifier is the new decision tree. Equations below show this hallmark:

$$F_0 = 0$$

$$F_t(x) = F_{t-1}(x) + h(x)$$

where h(x) is the new decision tree after $F_{t-1}(x)$ and $F_t(x)$ is the new model after t−1 steps. The objective of the XGBoost model is to find the tree $F_t(x)$ that minimizes the following equation at the $t^{th}$ step:

$$Obj(F_t) = L(F_{t-1} + F_t) + \Omega(F_t).$$

L is the loss function that decides the predictive power, and Ω is the regularization function controlling the overfitting.

In another implementation, the nutrition data generation system 424 is a convolutional neural network that processes the user images 432 and/or the food images 442 and produces the nutrition data 426.

A convolutional neural network is a special type of neural network. The fundamental difference between a densely connected layer and a convolution layer is this: Dense layers learn global patterns in their input feature space, whereas convolution layers learn local patterns: in the case of images, patterns found in small 2D windows of the inputs. This key characteristic gives convolutional neural networks two interesting properties: (1) the patterns they learn are translation invariant and (2) they can learn spatial hierarchies of patterns.

Regarding the first, after learning a certain pattern in the lower-right corner of a picture, a convolution layer can recognize it anywhere: for example, in the upper-left corner. A densely connected network would have to learn the pattern anew if it appeared at a new location. This makes convolutional neural networks data efficient because they need fewer training samples to learn representations they have generalization power.

Regarding the second, a first convolution layer can learn small local patterns such as edges, a second convolution layer will learn larger patterns made of the features of the first layers, and so on. This allows convolutional neural networks to efficiently learn increasingly complex and abstract visual concepts.

A convolutional neural network learns highly non-linear mappings by interconnecting layers of artificial neurons arranged in many different layers with activation functions that make the layers dependent. It includes one or more convolutional layers, interspersed with one or more sub-sampling layers and non-linear layers, which are typically followed by one or more fully connected layers. Each element of the convolutional neural network receives inputs from a set of features in the previous layer. The convolutional neural network learns concurrently because the neurons in the same feature map have identical weights. These local shared weights reduce the complexity of the network such that when multi-dimensional input data enters the network, the convolutional neural network avoids the complexity of data reconstruction in feature extraction and regression or classification process.

Convolutions operate over 3D tensors, called feature maps, with two spatial axes (height and width) as well as a depth axis (also called the channels axis). For an RGB image, the dimension of the depth axis is 3, because the image has three color channels; red, green, and blue. For a black-and-white picture, the depth is 1 (levels of gray). The convolution operation extracts patches from its input feature map and applies the same transformation to all of these patches, producing an output feature map. This output feature map is still a 3D tensor: it has a width and a height. Its depth can be arbitrary, because the output depth is a parameter of the layer, and the different channels in that depth axis no longer stand for specific colors as in RGB input; rather, they stand for filters. Filters encode specific aspects of the input data: at a height level, a single filter could encode the concept "presence of a face in the input," for instance.

For example, the first convolution layer takes a feature map of size (28, 28, 1) and outputs a feature map of size (26, 26, 32): it computes 32 filters over its input. Each of these 32 output channels contains a 26×26 grid of values, which is a response map of the filter over the input, indicating the response of that filter pattern at different locations in the input. That is what the term feature map means: every dimension in the depth axis is a feature (or filter), and the 2D tensor output [:, :, n] is the 2D spatial map of the response of this filter over the input.

Convolutions are defined by two key parameters: (1) size of the patches extracted from the inputs—these are typically 1×1, 3×3 or 5×5 and (2) depth of the output feature map—the number of filters computed by the convolution. Often these start with a depth of 32, continue to a depth of 64, and terminate with a depth of 128 or 256.

Figure 10:
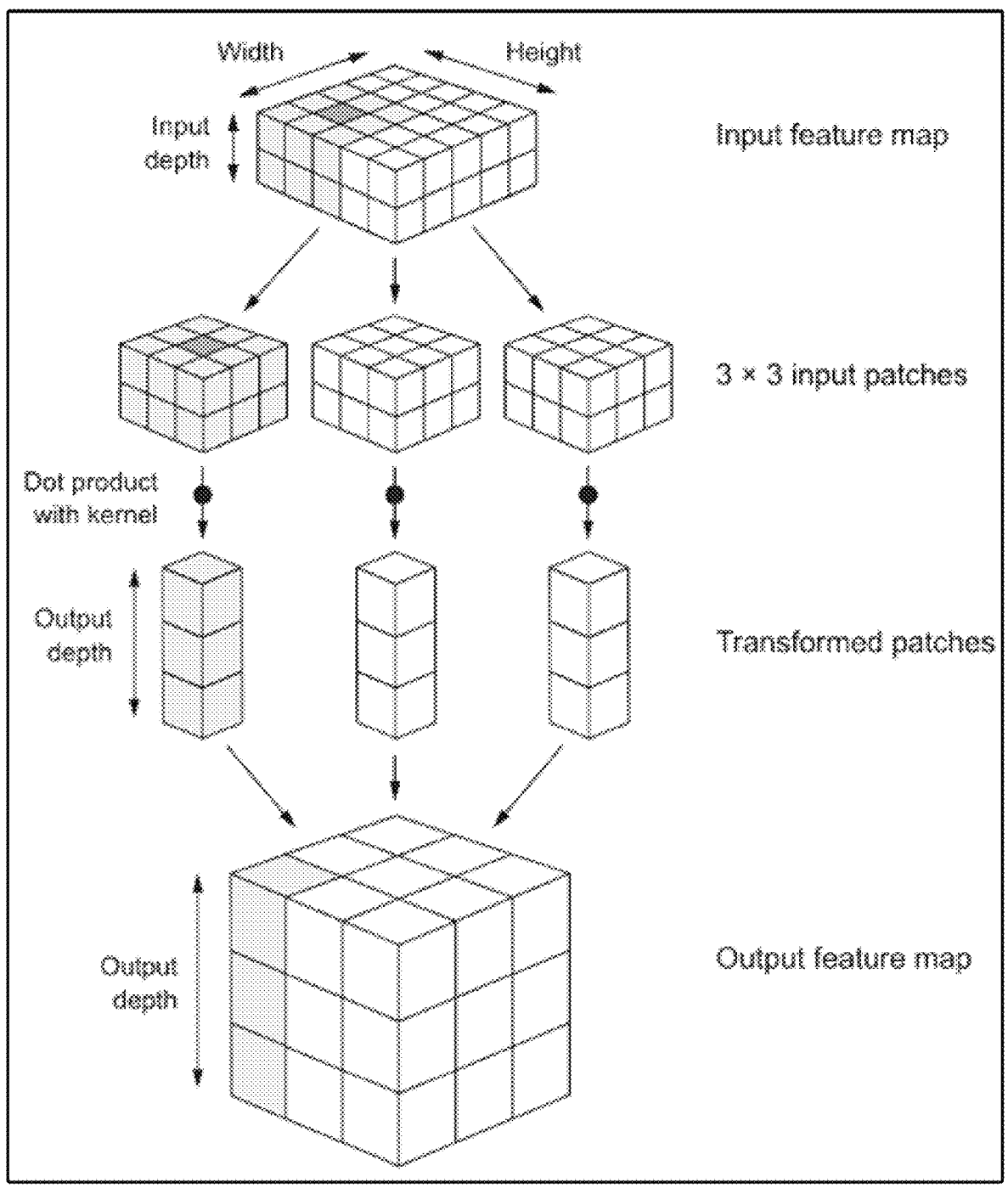
FIG. 10 depicts one implementation of workings of a convolutional neural network.

A convolution works by sliding these windows of size 3×3 or 5×5 over the 3D input feature map, stopping at every location, and extracting the 3D patch of surrounding features (shape (window_height, window_width, input_depth)). Each such 3D patch is ten transformed (via a tensor product with the same learned weight matrix, called the convolution kernel) into a 1D vector of shape (output_depth). All of these vectors are then spatially reassembled into a 3D output map of shape (height, width, output_depth). Every spatial location in the output feature map corresponds to the same location in the input feature map (for example, the lower-right corner of the output contains information about the lower-right corner of the input). For instance, with 3×3 windows, the vector output [i, j, :] comes from the 3D patch input [i−1:i+1, j−1:J+1, :]. The full process is detailed in FIG. 10.

The convolutional neural network comprises convolution layers which perform the convolution operation between the input values and convolution filters (matrix of weights) that are learned over many gradient update iterations during the training. Let (m, n) be the filter size and W be the matrix of weights, then a convolution layer performs a convolution of the W with the input X by calculating the dot product W·x+b, where x is an instance of X and b is the bias. The step size by which the convolution filters slide across the input is called the stride, and the filter area (m×n) is called the receptive field. A same convolution filter is applied across different positions of the input, which reduces the number of weights learned. It also allows location invariant learning, i.e., if an important pattern exists in the input, the convolution filters learn it no matter where it is in the sequence.

Training a Convolutional Neural Network

Figure 11:
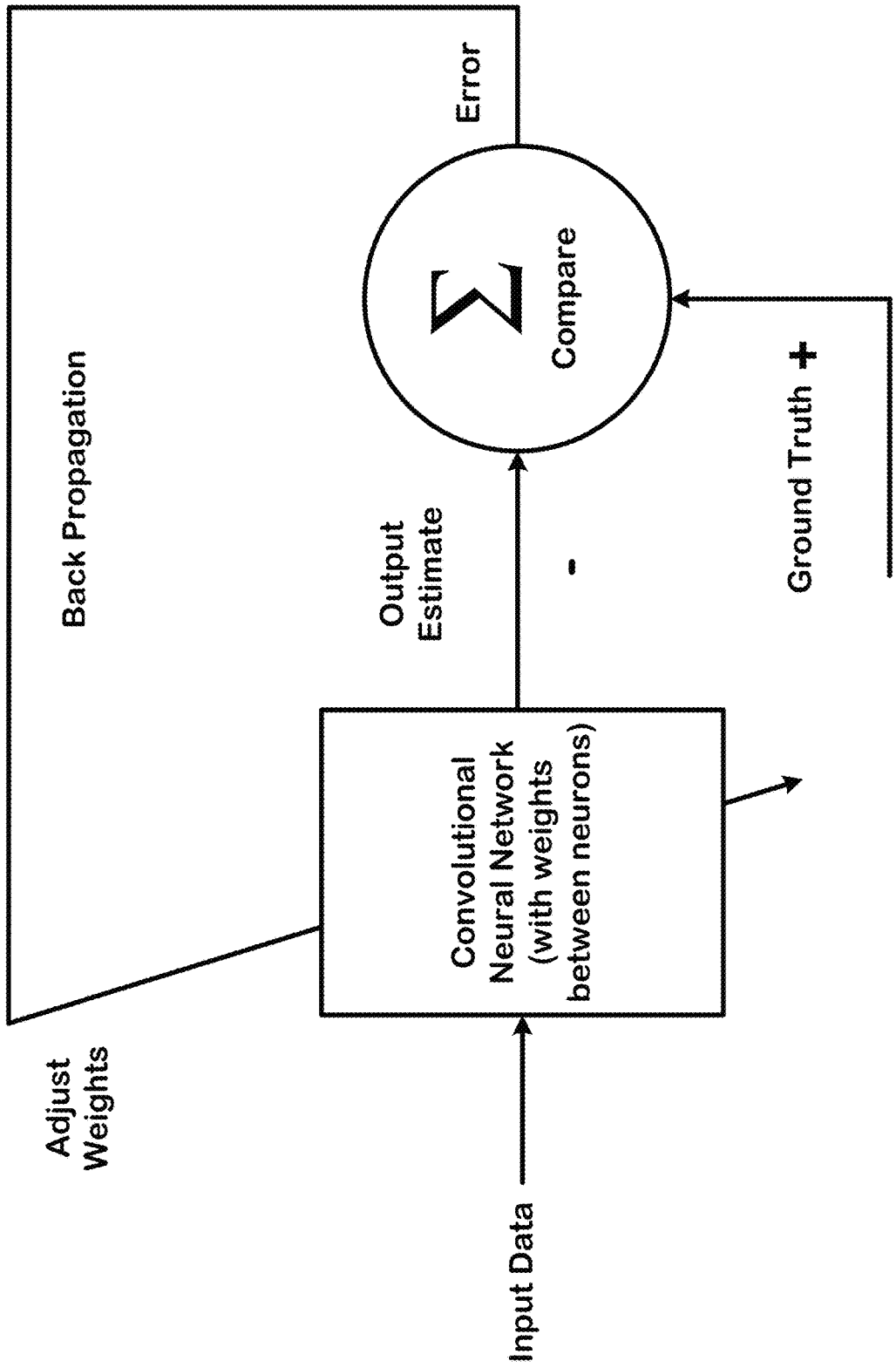
FIG. 11 depicts a block diagram of training a convolutional neural network in accordance with one implementation of the technology disclosed.

FIG. 11 depicts a block diagram of training a convolutional neural network in accordance with one implementation of the technology disclosed. The convolutional neural network is adjusted or trained so that the input data leads to a specific output estimate. The convolutional neural network is adjusted using back propagation based on a comparison of the output estimate and the ground truth until the output estimate progressively matches or approaches the ground truth.

The convolutional neural network is trained by adjusting the weights between the neurons based on the difference between the ground truth and the actual output. This is mathematically described as:

$$\Delta W_i = x_i \delta$$

where δ=(ground truth)−(actual output)

In one implementation, the training rule is defined as:

$$W_{nm} \leftarrow W_{nm} + \alpha(t_m - \varphi_m)a_n$$

In the equation above: the arrow indicates an update of the value; $t_m$ is the target value of neuron m; $\varphi_m$ is the computed current output of neuron m; $a_n$ is input n; and α is the learning rate.

The intermediary step in the training includes generating a feature vector from the input data using the convolution layers. The gradient with respect to the weights in each layer, starting at the output, is calculated. This is referred to as the backward pass, or going backwards. The weights in the network are updated using a combination of the negative gradient and previous weights.

In one implementation, the convolutional neural network uses a stochastic gradient update algorithm (such as ADAM) that performs backward propagation of errors by means of gradient descent. One example of a sigmoid function based back propagation algorithm is described below:

$$\varphi = f(h) = \frac{1}{1 + e^{-h}}$$

In the sigmoid function above, h is the weighted sum computed by a neuron. The sigmoid function has the following derivative:

$$\frac{\partial \varphi}{\partial h} = \varphi(1 - \varphi)$$

The algorithm includes computing the activation of all neurons in the network, yielding an output for the forward pass. The activation of neuron m in the hidden layers is described as:

$$\varphi_m = \frac{1}{1 + e^{-h_m}}$$

$$h_m = \sum_{n=1}^{N} a_n w_{nm}$$

This is done for all the hidden layers to get the activation described as:

$$\varphi_k = \frac{1}{1 + e^{h_k}}$$

$$h_k = \sum_{m=1}^{M} \varphi_m v_{mk}$$

Then, the error and the correct weights are calculated per layer. The error at the output is computed as:

$$\delta_{ok} = (t_k - \varphi_k)\varphi_k(1 - \varphi_k)$$

The error in the hidden layers is calculated as:

$$\delta_{hm} = \varphi_m(1-\varphi_m)\sum_{k=1}^{K} v_{mk}\delta_{ok}$$

The weights of the output layer are updated as:

$$v_{mk} \leftarrow v_{mk} + \alpha\delta_{ok}\varphi_m$$

The weights of the hidden layers are updated using the learning rate α as:

$$v_{nm} \leftarrow w_{nm} + \alpha\delta_{hm}a_n$$

In one implementation, the convolutional neural network uses a gradient descent optimization to compute the error across all the layers. In such an optimization, for an input feature vector x and the predicted output ŷ, the loss function is defined as l for the cost of predicting ŷ when the target is y, i.e. l (ŷ, y). The predicted output ŷ is transformed from the input feature vector x using function ƒ. Function ƒ is parameterized by the weights of convolutional neural network, i.e. ŷ=ƒ$_w$(x). The loss function is described as l (ŷ, y)=l (ƒ$_w$(x), y), or Q (z, w)=l (ƒ$_w$(x), y) where z is an input and output data pair (x, y). The gradient descent optimization is performed by updating the weights according to:

$$v_{t+1} = \mu v_t - \alpha\frac{1}{n}\sum_{i=1}^{N}\nabla w_t Q(z_t, w_t)$$

$$w_{t+1} = w_t + v_{t+1}$$

In the equations above, α is the learning rate. Also, the loss is computed as the average over a set of n data pairs. The computation is terminated when the learning rate α is small enough upon linear convergence. In other implementations, the gradient is calculated using only selected data pairs fed to a Nesterov's accelerated gradient and an adaptive gradient to inject computation efficiency.

In one implementation, the convolutional neural network uses a stochastic gradient descent (SGD) to calculate the cost function. A SGD approximates the gradient with respect to the weights in the loss function by computing it from only one, randomized, data pair, $Z_t$, described as:

$$V_{t+1} = \mu V_t - \alpha\nabla wQ(z_t, w_t)$$

$$W_{t+1} = W_t + V_{t+1}$$

In the equations above: α is the learning rate; μ is the momentum; and t is the current weight state before updating. The convergence speed of SGD is approximately O(1/t) when the learning rate α are reduced both fast and slow enough. In other implementations, the convolutional neural network uses different loss functions such as Euclidean loss and softmax loss. In a further implementation, an Adam stochastic optimizer is used by the convolutional neural network.

Convolution Layers

The convolution layers of the convolutional neural network serve as feature extractors. Convolution layers act as adaptive feature extractors capable of learning and decomposing the input data into hierarchical features. In one implementation, the convolution layers take two images as input and produce a third image as output. In such an implementation, convolution operates on two images in two-dimension (2D), with one image being the input image and the other image, called the "kernel", applied as a filter on the input image, producing an output image. Thus, for an input vector ƒ of length n and a kernel g of length m, the convolution ƒ*g of ƒ and g is defined as:

$$(f*g)(i) = \sum_{j=1}^{m} g(j)\cdot f(i-j+m/2)$$

The convolution operation includes sliding the kernel over the input image. For each position of the kernel, the overlapping values of the kernel and the input image are multiplied and the results are added. The sum of products is the value of the output image at the point in the input image where the kernel is centered. The resulting different outputs from many kernels are called feature maps.

Once the convolutional layers are trained, they are applied to perform recognition tasks on new inference data. Since the convolutional layers learn from the training data, they avoid explicit feature extraction and implicitly learn from the training data. Convolution layers use convolution filter kernel weights, which are determined and updated as part of the training process. The convolution layers extract different features of the input, which are combined at higher layers. The convolutional neural network uses a various number of convolution layers, each with different convolving parameters such as kernel size, strides, padding, number of feature maps and weights.

Non-Linear Layers

Figure 12:
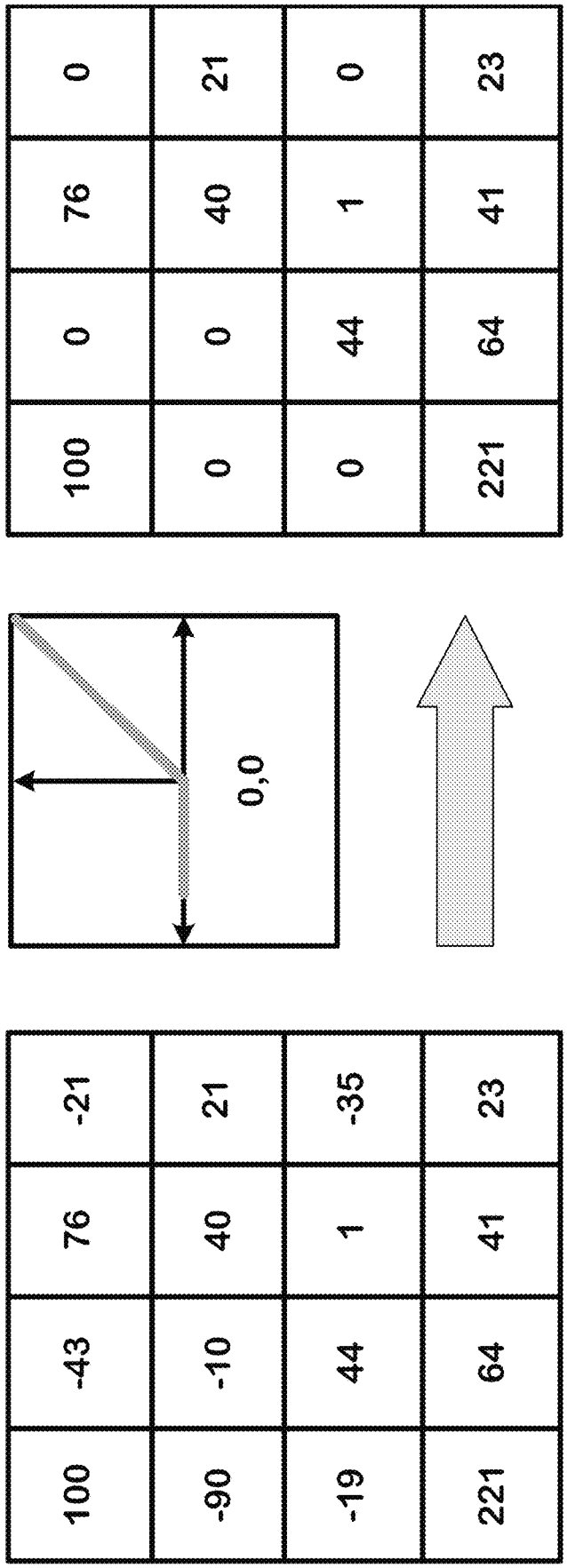
FIG. 12 shows one implementation of a ReLU non-linear layer in accordance with one implementation of the technology disclosed.

FIG. 12 shows one implementation of non-linear layers in accordance with one implementation of the technology disclosed. Non-linear layers use different non-linear trigger functions to signal distinct identification of likely features on each hidden layer. Non-linear layers use a variety of specific functions to implement the non-linear triggering, including the rectified linear units (ReLUs), hyperbolic tangent, absolute of hyperbolic tangent, sigmoid and continuous trigger (non-linear) functions. In one implementation, a ReLU activation implements the function y=max(x, 0) and keeps the input and output sizes of a layer the same. The advantage of using ReLU is that the convolutional neural network is trained many times faster. ReLU is a non-continuous, non-saturating activation function that is linear with respect to the input if the input values are larger than zero and zero otherwise. Mathematically, a ReLU activation function is described as:

$$\varphi(h) = \max(h, 0)$$

$$\varphi(h) = \begin{cases} h \text{ if } h > 0 \\ 0 \text{ if } h \leq 0 \end{cases}$$

In other implementations, the convolutional neural network uses a power unit activation function, which is a continuous, non-saturating function described by:

$$\varphi(h) = (a+bh)^c$$

In the equation above, a, b and c are parameters controlling the shift, scale and power respectively. The power activation function is able to yield x and y-antisymmetric activation if c is odd and y-symmetric activation if c is even. In some implementations, the unit yields a non-rectified linear activation.

In yet other implementations, the convolutional neural network uses a sigmoid unit activation function, which is a continuous, saturating function described by the following logistic function:

$$\varphi(h) = \frac{1}{1 + e^{-\beta h}}$$

In the equation above, β=1. The sigmoid unit activation function does not yield negative activation and is only antisymmetric with respect to the y-axis.

Dilated Convolutions

Figure 13:
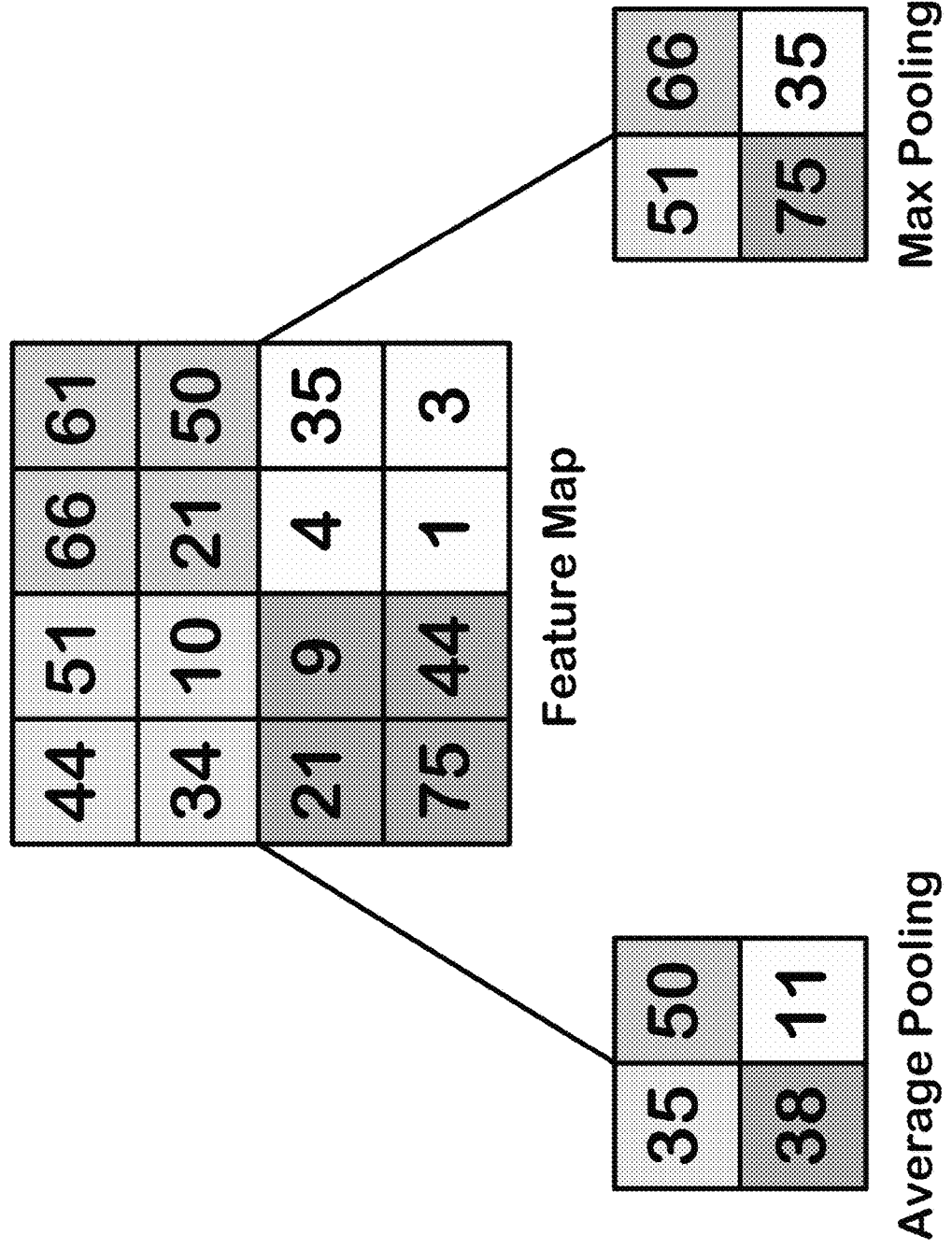
FIG. 13 illustrates dilated convolutions.

FIG. 13 illustrates dilated convolutions. Dilated convolutions, sometimes called atrous convolutions, which literally means with holes. The French name has its origins in the algorithme a trous, which computes the fast dyadic wavelet transform. In these type of convolutional layers, the inputs corresponding to the receptive field of the filters are not neighboring points. This is illustrated in FIG. 13. The distance between the inputs is dependent on the dilation factor.

Sub-Sampling Layers

Figure 14:
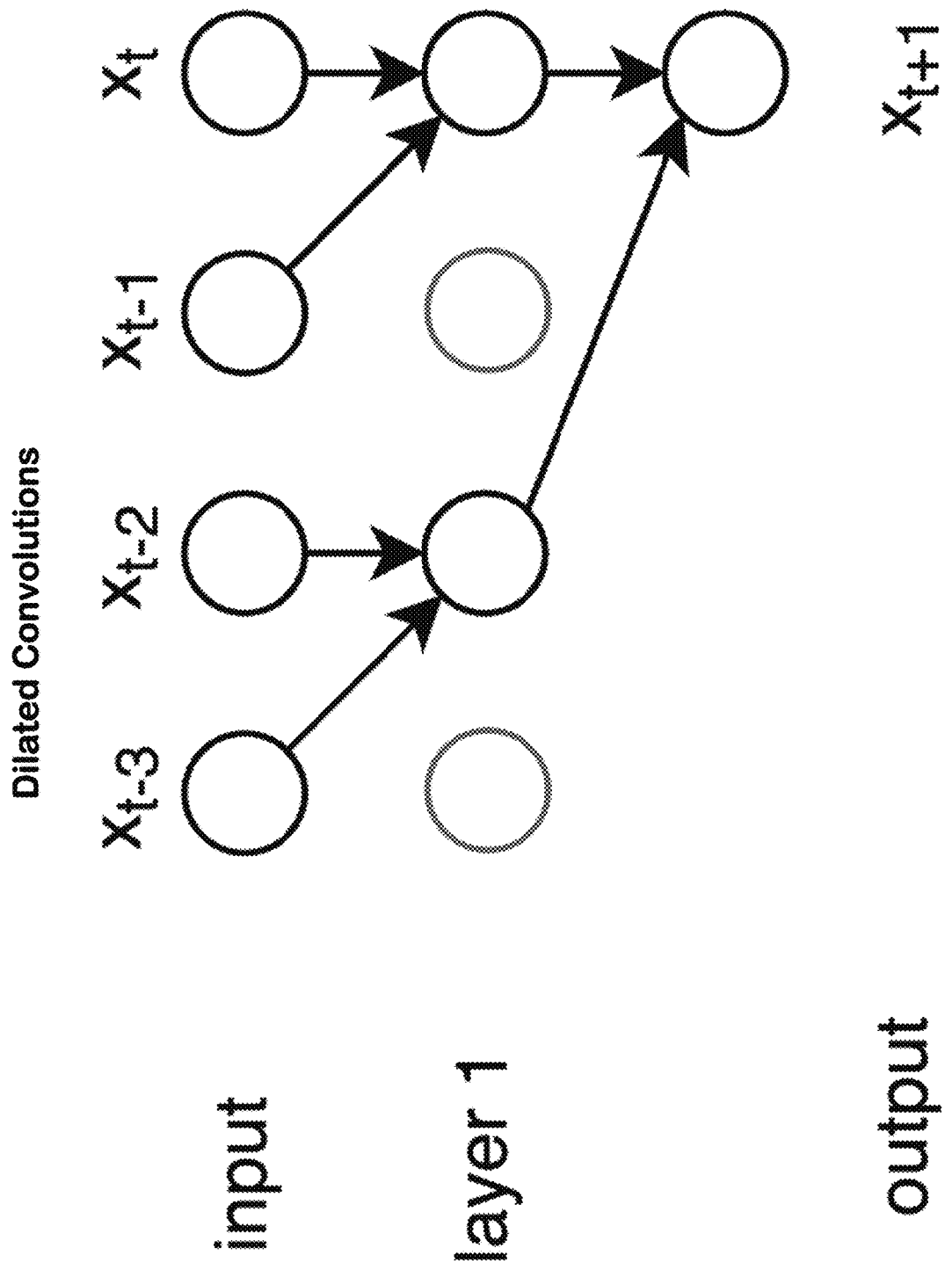
FIG. 14 is one implementation of sub-sampling layers (average/max pooling) in accordance with one implementation of the technology disclosed.

FIG. 14 is one implementation of sub-sampling layers in accordance with one implementation of the technology disclosed. Sub-sampling layers reduce the resolution of the features extracted by the convolution layers to make the extracted features or feature maps-robust against noise and distortion. In one implementation, sub-sampling layers employ two types of pooling operations, average pooling and max pooling. The pooling operations divide the input into non-overlapping two-dimensional spaces. For average pooling, the average of the four values in the region is calculated. For max pooling, the maximum value of the four values is selected.

In one implementation, the sub-sampling layers include pooling operations on a set of neurons in the previous layer by mapping its output to only one of the inputs in max pooling and by mapping its output to the average of the input in average pooling. In max pooling, the output of the pooling neuron is the maximum value that resides within the input, as described by:

$$\varphi_o = \max(\varphi_1, \varphi_2, \ldots, \varphi_N)$$

In the equation above, N is the total number of elements within a neuron set.

In average pooling, the output of the pooling neuron is the average value of the input values that reside with the input neuron set, as described by:

$$\varphi_o = \frac{1}{N}\sum_{n=1}^{N} \varphi_n$$

In the equation above, N is the total number of elements within input neuron set.

In FIG. 14, the input is of size 4×4. For 2×2 sub-sampling, a 4×4 image is divided into four non-overlapping matrices of size 2×2. For average pooling, the average of the four values is the whole-integer output. For max pooling, the maximum value of the four values in the 2×2 matrix is the whole-integer output.

Convolution Examples

Figure 15:
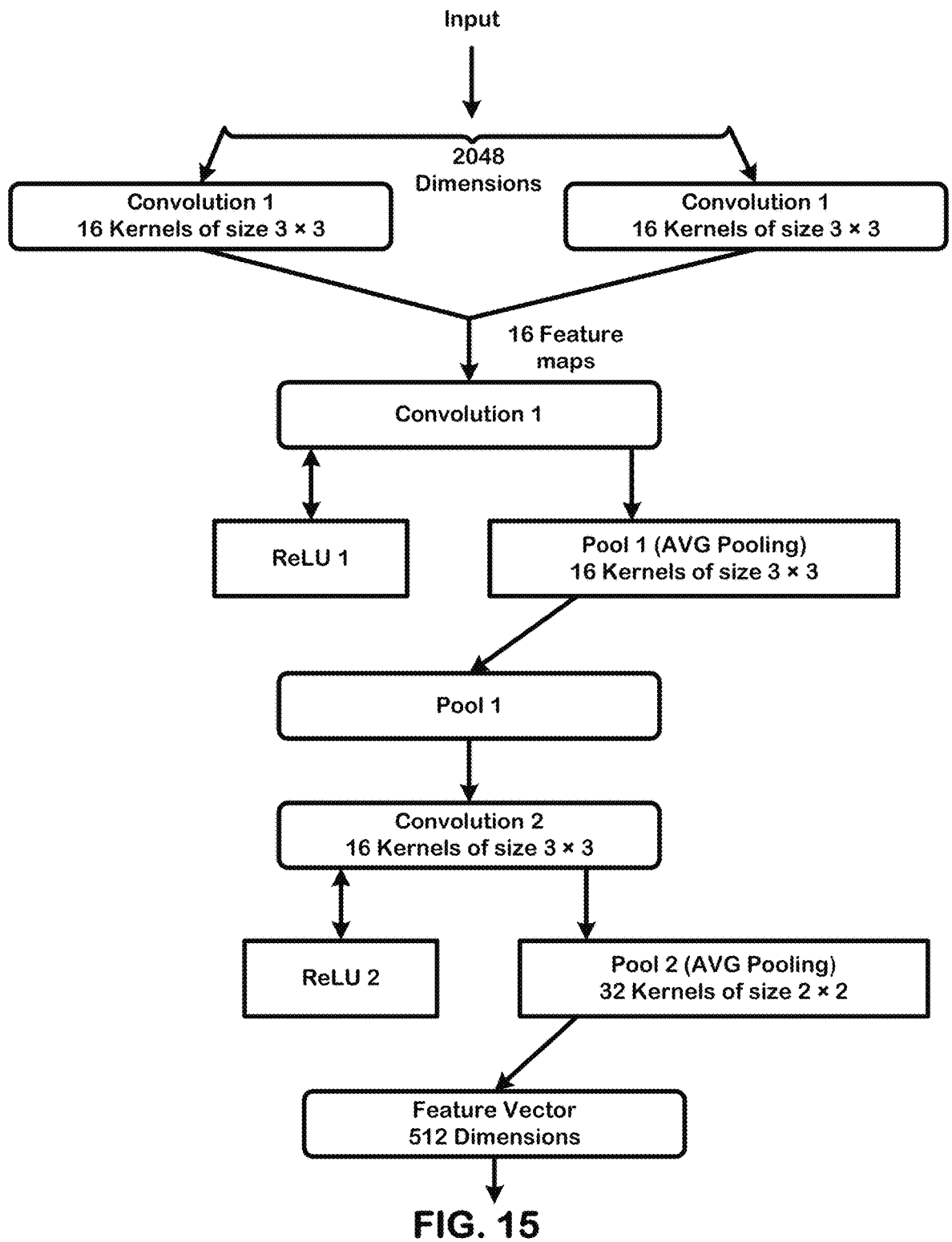
FIG. 15 depicts one implementation of a two-layer convolution of the convolution layers.

FIG. 15 depicts one implementation of a two-layer convolution of the convolution layers. In FIG. 15, an input of size 2048 dimensions is convolved. At convolution 1, the input is convolved by a convolutional layer comprising of two channels of sixteen kernels of size 3×3. The resulting sixteen feature maps are then rectified by means of the ReLU activation function at ReLU1 and then pooled in Pool 1 by means of average pooling using a sixteen channel pooling layer with kernels of size 3×3. At convolution 2, the output of Pool 1 is then convolved by another convolutional layer comprising of sixteen channels of thirty kernels with a size of 3×3. This is followed by yet another ReLU2 and average pooling in Pool 2 with a kernel size of 2×2. The convolution layers use varying number of strides and padding, for example, zero, one, two and three. The resulting feature vector is five hundred and twelve (512) dimensions, according to one implementation.

In other implementations, the convolutional neural network uses different numbers of convolution layers, sub-sampling layers, non-linear layers and fully connected layers. In one implementation, the convolutional neural network is a shallow network with fewer layers and more neurons per layer, for example, one, two or three fully connected layers with hundred (100) to two hundred (200) neurons per layer. In another implementation, the convolutional neural network is a deep network with more layers and fewer neurons per layer, for example, five (5), six (6) or eight (8) fully connected layers with thirty (30) to fifty (50) neurons per layer.

Forward Pass

The output of a neuron of row x, column y in the $l^{th}$ convolution layer and $k^{th}$ feature map for $f$ number of convolution cores in a feature map is determined by the following equation:

$$O_{x,y}^{(l,k)} = \tanh\left(\sum_{t=0}^{f-1}\sum_{r=0}^{k_h}\sum_{c=0}^{k_w} W_{(r,c)}^{(k,t)} O_{(x+r,x+c)}^{(l-1,t)} + \text{Bias}^{(l,k)}\right)$$

The output of a neuron of row x, column y in the $l^{th}$ sub-sample layer and $k^{th}$ feature map is determined by the following equation:

$$O_{x,y}^{(l,k)} = \tanh\left(W^{(k)}\sum_{r=0}^{S_h}\sum_{c=0}^{S_w} O_{(x\times S_h+r, y\times S_w+c)}^{(l-1,k)} + \text{Bias}^{(l,k)}\right)$$

The output of an $i^{th}$ neuron of the $l^{th}$ output layer is determined by the following equation:

$$O_{(l,i)} = \tanh\left(\sum_{j=0}^{H} O_{(l-1,j)} W_{(i,j)}^l j + \text{Bias}^{(l,i)}\right)$$

Backpropagation

The output deviation of a $k^{th}$ neuron in the output layer is determined by the following equation:

$$d(O_k^o) = y_k - t_k$$

The input deviation of a $k^{th}$ neuron in the output layer is determined by the following equation:

$$d(I_k^o) = (y_k - t_k)\varphi'(v_k) = \varphi'(v_k) d(O_k^o)$$

The weight and bias variation of a $k^{th}$ neuron in the output layer is determined by the following equation:

$$\Delta W_{k,x}{}^o = d(I_k{}^o) y_{k,x}$$

$$\Delta \text{Bias}_k{}^o = d(I_k{}^o)$$

The output bias of a $k^{th}$ neuron in the hidden layer is determined by the following equation:

$$d(O_k^H) = \sum_{i=0}^{i<84} d(I_i^o) W_{i,k}$$

The input bias of a $k^{th}$ neuron in the hidden layer is determined by the following equation:

$$d(I_k^H) = \varphi'(v_k) d(O_k^H)$$

The weight and bias variation in row x, column y in a $m^{th}$ feature map of a prior layer receiving input from k neurons in the hidden layer is determined by the following equation:

$$\Delta W_{m,x,y}{}^{H,k} = d(I_k^H) y_{x,y}{}^m$$

$$\Delta \text{Bias}_k{}^H = d(I_k^H)$$

The output bias of row x, column y in a $m^{th}$ feature map of sub-sample layer S is determined by the following equation:

$$d(O_{x,y}^{S,m}) = \sum_{k}^{170} d(I_{m,x,y}^H) W_{m,x,y}^{H,k}$$

The input bias of row x, column y in a $m^{th}$ feature map of sub-sample layer S is determined by the following equation:

$$d(I_{x,y}^{S,m}) = \varphi'(v_k) d(O_{x,y}^{S,m})$$

The weight and bias variation in row x, column y in a $m^{th}$ feature map of sub-sample layer S and convolution layer C is determined by the following equation:

$$\Delta W^{S,m} = \sum_{x=0}^{fh} \sum_{y=0}^{fw} d(I_{[x/2],[y/2]}^{S,m}) O_{x,y}^{C,m}$$

$$\Delta \text{Bias}^{S,m} = \sum_{x=0}^{fh} \sum_{y=0}^{fw} d(O_{x,y}^{S,m})$$

The output bias of row x, column y in a $k^{th}$ feature map of convolution layer C is determined by the following equation:

$$d(O_{x,y}^{C,k}) = d(I_{[x/2],[y/2]}^{S,k}) W^*$$

The input bias of row x, column y in a $k^{th}$ feature map of convolution layer C is determined by the following equation:

$$d(I_{x,y}^{C,k}) = \varphi'(v_k) d(O_{x,y}^{C,k})$$

The weight and bias variation in row r, column c in an $m^{th}$ convolution core of a $k^{th}$ feature map of $l^{th}$ convolution layer C:

$$\Delta W_{r,c}^{k,m} = \sum_{x=0}^{fh} \sum_{y=0}^{fw} d(I_{x,y}^{C,k}) O_{x+r,y+c}^{l-1,m}$$

-continued $$\Delta \text{Bias}^{C,k} = \sum_{x=0}^{fh} \sum_{y=0}^{fw} d(I_{x,y}^{C,k})$$

In one implementation, the nutrition data 426 further comprises amount of processed food servings, amount of natural food, amount of organic food, amount of genetically modified organism food, amount of net protein, amount of net carbohydrate, amount of net fat, amount of net transfat, amount of net saturated fat, amount of net high-density cholesterol, amount of net low-density cholesterol, amount of net vitamin A, amount of net vitamin B, amount of net vitamin C, amount of net vitamin D, amount of net vitamin E, amount of net iron, amount of net sodium, amount of net calcium, amount of net magnesium, amount of net potassium, and amount of net fiber.

FIG. 5 shows one implementation of the data processing system 502. The data processing system 502 processes the avatar data 138, the user data 306, and the nutrition data 426 and produces environment interaction data 512.

FIG. 6 depicts one example of the environment interaction data 512. The environment interaction data 512 includes (i) metadata 602 about the food offerings and the avatar's response 612 to the food offerings, (ii) time spent 622 by the avatar in different health states, and (iii) the avatar's fitness 632.

In one implementation, the metadata 602 about the food offerings further comprises frequency of food presented to the avatar in the digital vaccine environment, mathematical pattern of food choices presented to the avatar in the digital vaccine environment, and velocity of food choices presented to the avatar in the digital vaccine environment.

In another implementation, the metadata 602 about the avatar's response to the food offerings further comprises number of interactions the avatar has with healthy food in the digital vaccine environment, number of interactions the avatar has with pseudo-healthy food in the digital vaccine environment, number of interactions the avatar has with unhealthy food in the digital vaccine environment, duration of the interactions, and velocity vector of the interactions.

In one implementation, the time spent 622 by the avatar in different health states further comprises total time spent by the avatar at the different stages of the digital vaccine environment, total time spent by the avatar in a fit health state, total time spent by the avatar in a danger health state, and total time spent by the avatar in an unhealthy health state.

In one implementation, the avatar's fitness 632 further comprises avatar's movement speed.

FIG. 7 shows one implementation of the modification system 702. The modification system 702 modifies parameters 712 of the digital vaccine environment 100, the avatar 126, and the stages 108 based on the environment interaction data 512.

The parameters 712 of the digital vaccine environment 100, the avatar 126, and the stages 108 further comprise number of enemies in the digital vaccine environment, number of robots Non player characters (NPCs) in the digital vaccine environment, strength of the enemy NPCs, type of the enemy NPCs, percentage of enemy enemy NPCs, type of friendly NPC pets, accuracy of enemy NPCs, velocity of enemy NPCs, virtual food spawn location, levels and two-dimensional (2D) and three-dimensional augment reality and virtual reality assets selection, neurocognitive training module selection, nutrition facts module, game level up menu, avatar mesh shape, leaderboard on/off, avatar powerup menu on/off, avatar customization marketplace, game feature reconfiguration setting, level of virtual target selection, level of real-world target selection, and score target.

The data processing system 502 and the modification system 702 can be any type of machine learning systems and can be trained to configure the parameters 712 of the digital vaccine environment 100, the avatar 126, and the stages 108. The training can be supervised, unsupervised, and/or semi-supervised. Some examples of the machine learning systems that can be used by the data processing system 502 and the modification system 702 include support vector machines, discriminant analysis, naïve bayes, nearest neighbor, decision trees, K-means, hierarchical, gaussian mixture, hidden markov model, eXtreme Gradient Boosted trees, and neural networks. Also, the different types of neural networks that can be used by the data processing system 502 and the modification system 702 are listed in FIG. 17.

Figure 16:
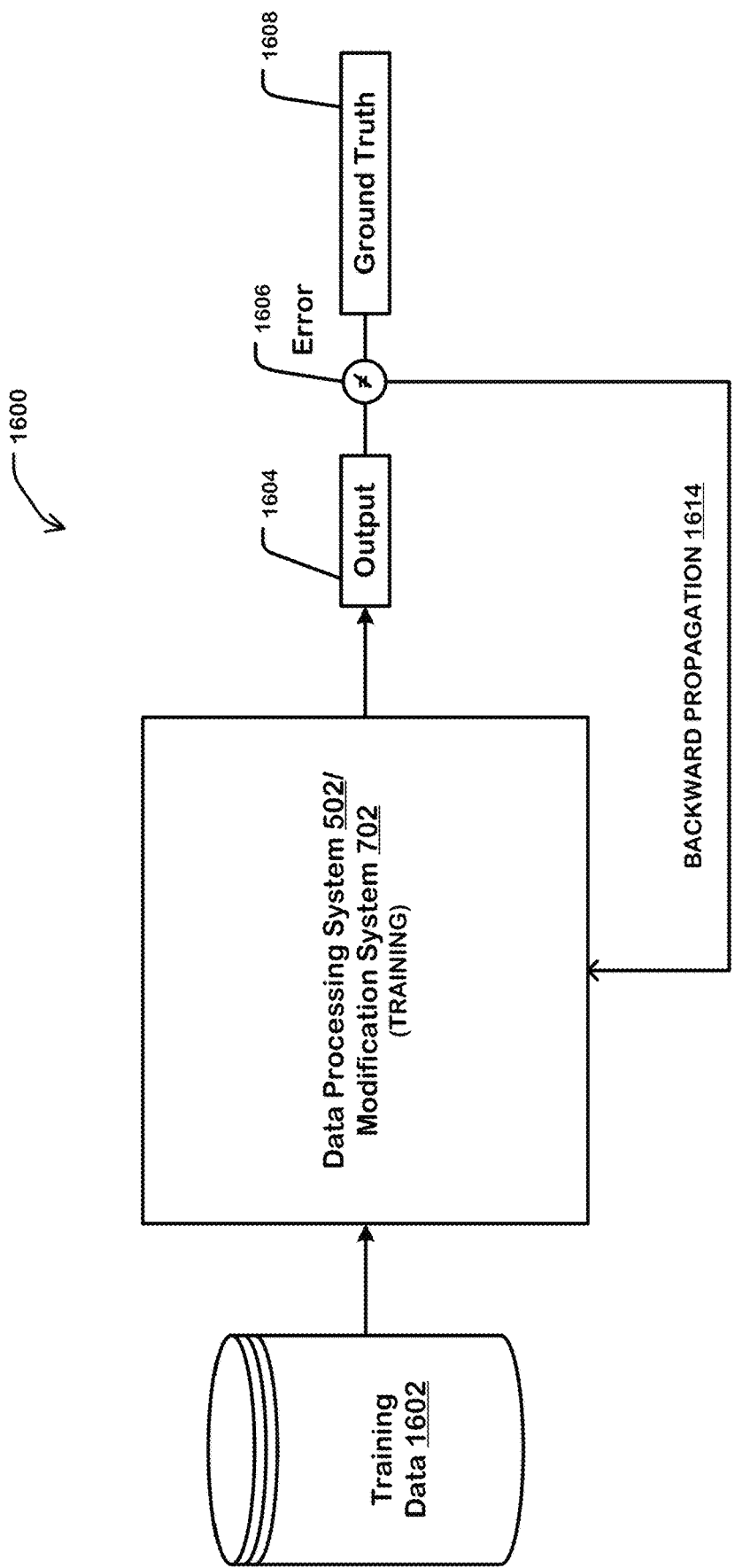
FIG. 16 illustrates one implementation of a training stage in which the data processing system and the modification system are trained.

FIG. 16 illustrates one implementation of a training stage in which the data processing system 502 and the modification system 702 are trained on training data to configure the parameters 712 of the digital vaccine environment 100, the avatar 126, and the stages 108. The goal of training the data processing system 502 and the modification system 702 is optimization of the weight parameters in each layer, which gradually combines simpler features into complex features so that the most suitable hierarchical representations can be learned from the training data. A single cycle 1600 of the optimization process is organized as follows. First, given a training dataset 1602 to the data processing system 502 and the modification system 702 under training, the forward pass sequentially computes the output 1604 in each layer and propagates the function signals forward through the network. In the final output layer, an objective loss function measures error 1606 between the inferenced outputs 1604 and the ground truth 1608.

To minimize the prediction error, the backward pass 1614 uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, eXtreme Gradient Boosting can provide stochastic approximations by performing the updates for each small set of data examples. In some implementations, the data processing system 502 and the modification system 702 is trained on a training data set of at least a hundred thousand examples of paired ground truth using a backpropagation-based gradient update technique.

Figure 18:
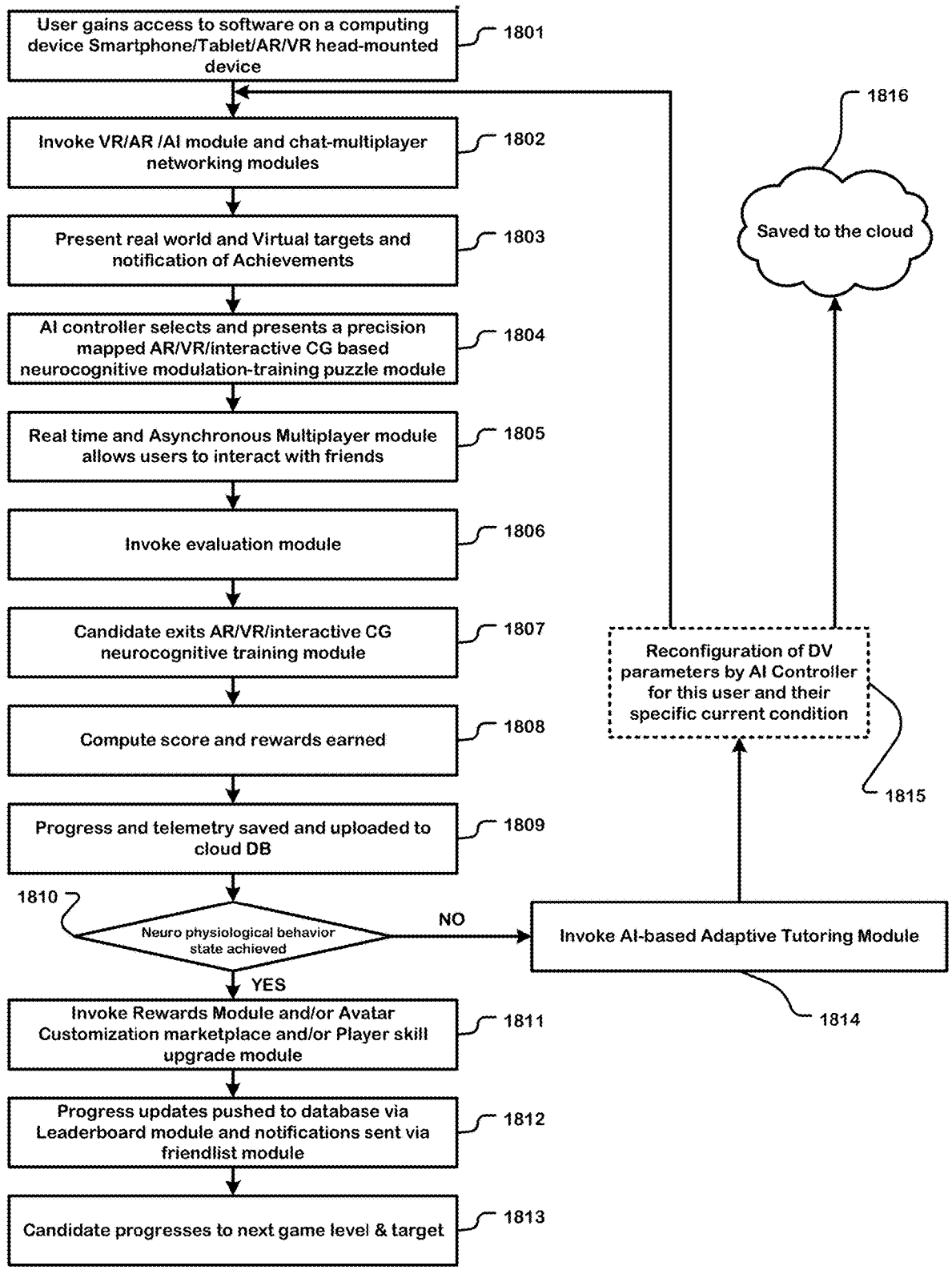
FIG. 18 depicts one implementation of a method for artificial intelligence-controlled neuro physiological-behavior state modulation to lower health risk score.

FIG. 18 depicts one implementation of a method for artificial intelligence-controlled neuro physiological-behavior state modulation to lower health risk score.

At action 1801, user gains access to software on a computing device Smartphone/Tablet/AR/VR head-mounted device.

At action 1802, the digital vaccine environment 100 invokes VR/AR/AI module and chat-multiplayer networking modules.

At action 1803, the digital vaccine environment 100 presents, to the users, real world and virtual targets and notification of achievements.

At action 1804, the AI controller of the digital vaccine environment 100 selects and presents a precision mapped AR/VR/interactive CG based neurocognitive modulation-training puzzle module.

At action 1805, the real time and asynchronous multiplayer module of the digital vaccine environment 100 allows the users to interact with friends.

At action 1806, the digital vaccine environment 100 invokes evaluation module.

At action 1807, the candidate exits AR/VR/interactive CG neurocognitive training module.

At action 1808, the digital vaccine environment 100 computes score and rewards earned.

At action 1809, the digital vaccine environment 100 progresses to the next stage and saves the telemetry and uploads it to a cloud database.

At action 1810, the digital vaccine environment 100 checks whether the desired neurobehavior state has been achieved.

At action 1811, if the desired neuro physiological-behavior state has been achieved, then the digital vaccine environment 100 invokes rewards module and/or avatar customization marketplace and/or player skill upgrade module.

At action 1812, the digital vaccine environment 100 pushes updates to database via a leaderboard module and send notifications via a friend-list module.

At action 1813, the candidate progresses to the next game level and target.

At action 1814, if the desired neuro physiological behavior state has not been achieved, then the digital vaccine environment 100 invokes an AI-based adaptive tutoring module.

At action 1815, the AI-based adaptive tutoring module then reconfigures parameters of the digital vaccine environment 100 for this user and her specific current condition.

At action 1816, the reconfigured parameters of the digital vaccine environment 100 are saved into the cloud database.

Figure 19:
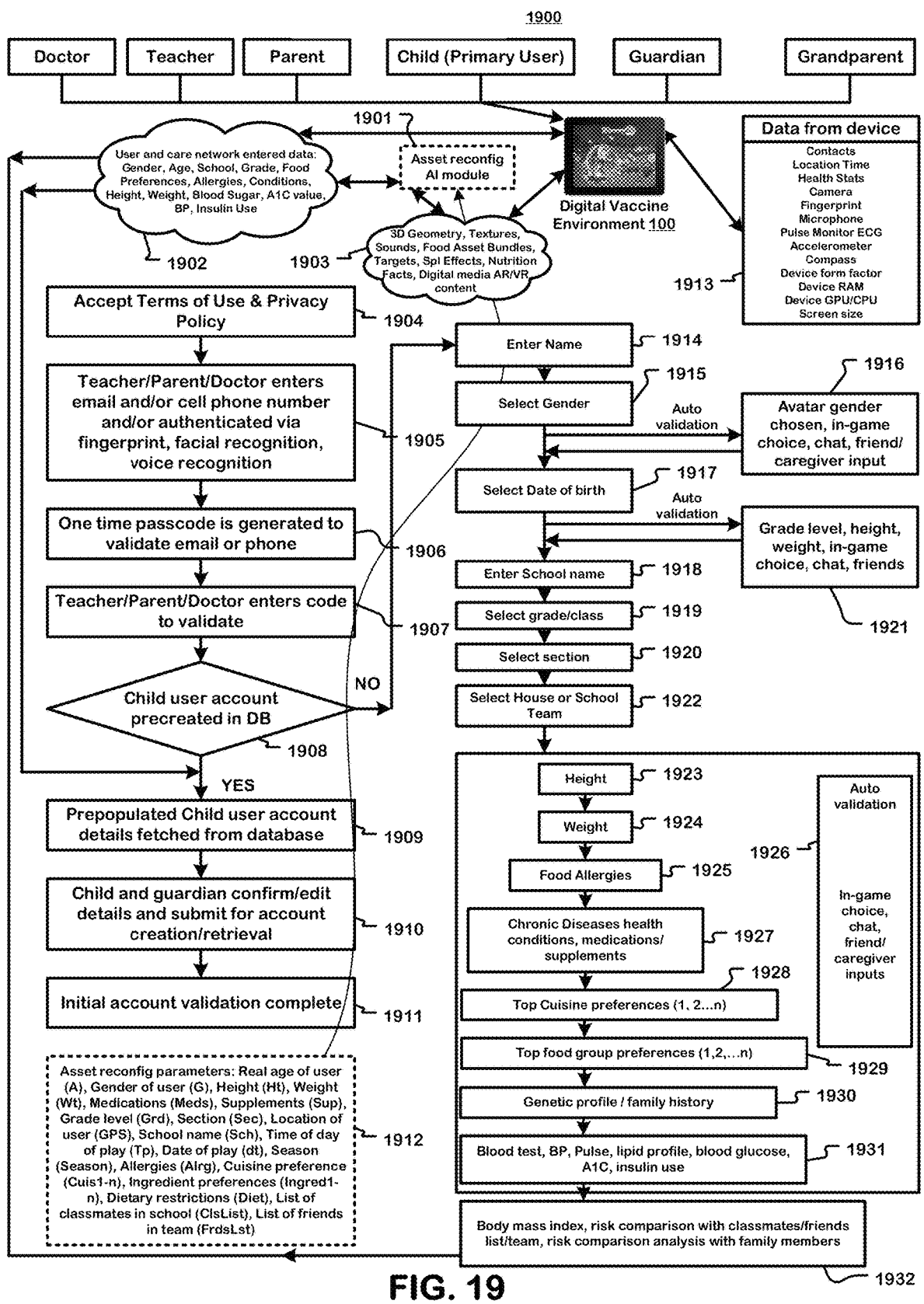
FIG. 19 depicts one implementation of a method for personalization of precision health risk mapping.

FIG. 19 depicts one implementation of a method for personalization of precision health risk mapping.

User data can be entered into the digital vaccine environment 100 by any of the entities 1900 listed in FIG. 19.

At action 1904, the entity accepts terms of use and privacy policy.

At action 1905, the teacher/parent/doctor enters email and/or cell phone number and/or authentication is done via fingerprint, facial recognition, voice recognition.

At action 1906, one time passcode is generated to validate email or phone.

At action 1907, the teacher/parent/doctor enters code to validate.

At action 1908, a determination is made whether the child user account already exists in the database.

At action 1909, if the child user account already exists in the database, then the child user account is prepopulated with details fetched from database.

At action 1910, then the child and guardian confirms/edits details and submits for account creation/retrieval.

At action 1911, the initial account validation is complete.

At action 1912, various asset parameters are reconfigured.

At action 1913, the asset parameters are provided as input to the asset reconfiguration AI module 1901 to generate parameters 1903 of the digital vaccine environment 100. Similarly, the child user information 1902 is provided as input to the asset reconfiguration AI module 1901 to further generate parameters 1903 of the digital vaccine environment 100. Additionally, the digital vaccine environment 100 is configured with data from the device 1913.

If the child user account does not exist in the database, then the child name (1914), the child gender (1915), the child date of birth (1917), the child school name (1918), the child grade/class (1919), the child class section (1920), and the child house or school team (1922) are identified to and specified in the digital vaccine environment 100.

At action 1916, auto-validation maps the child user characteristics and initializes the avatar with corresponding gender, in-game choice, chat, and friend/caregiver input, i.e., assets of the digital vaccine environment 100.

At action 1921, auto-validation maps the child user characteristics and initializes the game (the digital vaccine environment 100) with corresponding game level and the child user characteristics.

Finally, additional child user information such as height (1923), weight (1924), food allergies (1925), chronic diseases health conditions, medications/supplements (1927), cuisine preferences (1928), food group preferences (1929), genetic profile/family history (1930), clinical tests results (1931) are used for auto-validation of the digital vaccine environment 100.

At action 1932, the body mass index and risk are compared with classmates/friends list/team and with family members.

Computer System

FIG. 20 is a simplified block diagram of a computer system 2000 that can be used to implement the technology disclosed. Computer system 2000 includes at least one central processing unit (CPU) 2072 that communicates with a number of peripheral devices via bus subsystem 2055. These peripheral devices can include a storage subsystem 2010 including, for example, memory devices and a file storage subsystem 2036, user interface input devices 2038, user interface output devices 2076, and a network interface subsystem 2074. The input and output devices allow user interaction with computer system 2000. Network interface subsystem 2074 provides an interface to outside networks, including an interface to corresponding interface devices in other computer systems.

In one implementation, the data processing system 502 and/or the modification system 702 are communicably linked to the storage subsystem 2010 and the user interface input devices 2038.

User interface input devices 2038 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 2000.

User interface output devices 2076 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 2000 to the user or to another machine or computer system.

Storage subsystem 2010 stores programming and data constructs that provide the functionality of some or all of the modules and methods described herein. Subsystem 2078 can be graphics processing units (GPUs) or field-programmable gate arrays (FPGAs).

Memory subsystem 2022 used in the storage subsystem 2010 can include a number of memories including a main random access memory (RAM) 2032 for storage of instructions and data during program execution and a read only memory (ROM) 2034 in which fixed instructions are stored. A file storage subsystem 2036 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 2036 in the storage subsystem 2010, or in other machines accessible by the processor.

Bus subsystem 2055 provides a mechanism for letting the various components and subsystems of computer system 2000 communicate with each other as intended. Although bus subsystem 2055 is shown schematically as a single bus, alternative implementations of the bus subsystem can use multiple busses.

Computer system 2000 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 2000 depicted in FIG. 20 is intended only as a specific example for purposes of illustrating the preferred embodiments of the present invention. Many other configurations of computer system 2000 are possible having more or less components than the computer system depicted in FIG. 20.

Clauses

The following clauses are disclosed herein:

1. A digital vaccine system, comprising:

a digital vaccine environment which presents a user-driven avatar with (i) tasks that test the avatar's physical fitness and (ii) food offerings at various stages, wherein the avatar's appearance is responsive to the avatar's performance on the tasks and selection of the food offerings;

an input generation system with a virtual input generation sub-system and an actual input generation sub-system, wherein the virtual input generation sub-system monitors the avatar's progression through the digital vaccine environment and produces avatar data, including (i) avatar food preference data, (ii) avatar calorie data, (iii) avatar insulin data, (iv) avatar glucose data, (v) avatar A1C data, (vi) avatar ketone data, (vii) avatar cholesterol (HDL/LDL) data, (viii) avatar amino acid data, (ix) avatar glycoprotein acetyls data, and (x) avatar gut microbiome data and the actual input generation sub-system accesses a user information database and produces user data, including (i) user food preference data, (ii) user calorie data, (iii) user glycemic data, (iv) user insulin data, (v) user glucose data, (vi) user A1C data, (vii) user ketone data, (viii) user cholesterol (HDL/LDL) data, (ix) user amino acid data, (x) user glycoprotein acetyls data, and (xi) user microbiome data;

a nutrition data generation system that processes (i) food logs, (ii) user conversation files, (iii) user images, and/or (iv) food images and produces nutrition data;

a data processing system that processes the avatar data, the user data, and the nutrition data and produces environment interaction data, including (i) metadata about the food offerings and the avatar's response to the food offerings, (ii) time spent by the avatar in different health states, and (iii) the avatar's fitness; and a modification system that modifies parameters of the digital vaccine environment, the avatar, and the stages based on the environment interaction data.

2. The digital vaccine system of clause 1, wherein
the avatar food preference data further comprises
time stamped virtual food presented to the avatar in the digital vaccine environment, and
time stamped virtual food selected by the avatar in the digital vaccine environment;
the avatar calorie data further comprises
total calorie level of the avatar,
calories expanded by the avatar as a result of performing the tasks, and
net calorie level of the avatar;
the avatar insulin data further comprises
virtual insulin dose counter, and
virtual insulin units;
the avatar glucose data further comprises
virtual net blood glucose;
the avatar A1C data further comprises
virtual A1C results;
the avatar ketone data further comprises
virtual ketone level;
the avatar cholesterol data further comprises
virtual LDL/HDL level;
the avatar amino acid data further comprises
virtual amino acid level;
the avatar gut microbiome data further comprises
virtual microbiome level; and
the avatar glycoprotein acetyl data further comprises
virtual glycoprotein acetyls level;

3. The digital vaccine system of clause 1, wherein
the user food preference data further comprises
time stamped actual food presented to the user in real world, and
time stamped actual food consumed by the user in the real world;
the user calorie data further comprises
actual calories consumed by the user in the real world, and
calories expanded by the user in the real world;
the user glycemic data further comprises
glycemic index, and
glycemic load;
the user insulin data further comprises
actual insulin dose counter, and
actual insulin units;
the user glucose data further comprises
actual net blood glucose;
the user A1C data further comprises
actual A1C results;
the user ketone data further comprises
actual ketone level;
the user cholesterol data further comprises
actual LDL/HDL level;
the user amino acid data further comprises
actual amino acid level;
the user gut microbiome data further comprises
actual microbiome level; and
the user glycoprotein acetyls data further comprises
actual glycoprotein acetyls level.

4. The digital vaccine system of clause 1, wherein the nutrition data generation system is a recurrent neural network that processes the user conversation files and produces the nutrition data.

5. The digital vaccine system of clause 1, wherein the nutrition data generation system is a convolutional neural network that processes the user images and/or the food images and produces the nutrition data.

6. The digital vaccine system of clause 1, wherein the nutrition data further comprises:
amount of processed food servings,
amount of natural food,
amount of organic food,
amount of genetically modified organism food,
amount of net protein,
amount of net carbohydrate,
amount of net fat,
amount of net transfat,
amount of net saturated fat,
amount of net high-density cholesterol,
amount of net low-density cholesterol,
amount of net vitamin A,
amount of net vitamin B,
amount of net vitamin C,
amount of net vitamin D,
amount of net vitamin E,
amount of net iron,
amount of net sodium,
amount of net calcium,
amount of net magnesium,
amount of net potassium, and
amount of net fiber.

7. The digital vaccine system of clause 1, wherein the metadata about the food offerings further comprises:
frequency of food presented to the avatar in the digital vaccine environment,
mathematical pattern of food choices presented to the avatar in the digital vaccine environment, and
velocity of food choices presented to the avatar in the digital vaccine environment.

8. The digital vaccine system of clause 1, wherein the metadata about the avatar's response to the food offerings further comprises:
number of interactions the avatar has with healthy food in the digital vaccine environment,
number of interactions the avatar has with pseudo-healthy food in the digital vaccine environment,
number of interactions the avatar has with unhealthy food in the digital vaccine environment,
duration of the interactions, and
velocity vector of the interactions.

9. The digital vaccine system of clause 1, wherein the time spent by the avatar in different health states further comprises:
total time spent by the avatar at the different stages of the digital vaccine environment,
total time spent by the avatar in a fit health state,
total time spent by the avatar in a danger health state, and
total time spent by the avatar in an unhealthy health state.

10. The digital vaccine system of clause 1, wherein the avatar's fitness further comprises:
avatar's movement speed.

11. The digital vaccine system of clause 1, wherein the parameters of the digital vaccine environment, the avatar, and the stages further comprise:
number of enemies in the digital vaccine environment,
number of enemy Non player characters NPCs in the digital vaccine environment,
strength of the enemy NPCs,
type of the enemy NPCs,
percentage of enemy NPCs,
type of friendly NPCs,
accuracy of enemy NPCs, accuracy of friendly NPCs
velocity of NPCs,
virtual food spawn location,
levels and two-dimensional (2D) and three-dimensional augment reality and virtual reality assets selection,
neurocognitive training module selection,
nutrition facts module,
game level up menu,
avatar mesh shape,
leaderboard on/off,
avatar powerup menu on/off,
avatar customization marketplace,
game feature reconfiguration setting,
level of virtual target selection,
level of real-world target selection, and
score target.

12. A computer-implemented method of providing a digital vaccine system, including:
presenting a user-driven avatar with (i) tasks that test the avatar's physical fitness and (ii) food offerings at various stages, wherein the avatar's appearance is responsive to the avatar's performance on the tasks and selection of the food offerings;
monitoring the avatar's progression through the digital vaccine environment and producing avatar data, including (i) avatar food preference data, (ii) avatar calorie data, (iii) avatar insulin data, (iv) avatar glucose data, (v) avatar A1C data, and (vi) avatar ketone data, (vii) avatar cholesterol (HDL/LDL) data, (viii) avatar amino acid data, (ix) avatar glycoprotein acetyls data, and (x) avatar gut microbiome data and
accessing a user information database and producing user data, including (i) user food preference data, (ii) user calorie data, (iii) user glycemic data, (iv) user insulin data, (v) user glucose data, (vi) user A1C data, and (vii) user ketone data, (viii) user cholesterol (HDL/LDL) data, (ix) user amino acid data, (x) user glycoprotein acetyls data, and (xi) user microbiome data;
processing (i) food logs, (ii) user conversation files, (iii) user images, and/or (iv) food images and producing nutrition data;
processing the avatar data, the user data, and the nutrition data and producing environment interaction data, including (i) metadata about the food offerings and the avatar's response to the food offerings, (ii) time spent by the avatar in different health states, and (iii) the avatar's fitness; and
modifying parameters of the digital vaccine environment, the avatar, and the stages based on the environment interaction data.

13. The computer-implemented method of clause 12, wherein
the avatar food preference data further comprises
time stamped virtual food presented to the avatar in the digital vaccine environment, and
time stamped virtual food selected by the avatar in the digital vaccine environment; the avatar calorie data further comprises
total calorie level of the avatar,
calories expanded by the avatar as a result of performing the tasks, and
net calorie level of the avatar;
the avatar insulin data further comprises
virtual insulin dose counter, and
virtual insulin units;
the avatar glucose data further comprises
virtual net blood glucose;
the avatar A1C data further comprises
virtual A1C results;
the avatar ketone data further comprises
virtual ketone level;
the avatar cholesterol data further comprises
virtual LDL/HDL level;
the avatar amino acid data further comprises
virtual amino acid level;
the avatar gut microbiome data further comprises
virtual microbiome level; and
the avatar glycoprotein acetyl data further comprises
virtual glycoprotein acetyls level.

14. The computer-implemented method of clause 12, wherein
the user food preference data further comprises
time stamped actual food presented to the user in real world, and
time stamped actual food consumed by the user in the real world;
the user calorie data further comprises
actual calories consumed by the user in the real world,
calories expanded by the user in the real world;
the user glycemic data further comprises
glycemic index, and
glycemic load;
the user insulin data further comprises
actual insulin dose counter, and
actual insulin units;
the user glucose data further comprises
actual net blood glucose;
the user A1C data further comprises
actual A1C results;
the user ketone data further comprises
actual ketone level;
the user cholesterol data further comprises
actual LDL/HDL level;
the user amino acid data further comprises
actual amino acid level;
the user gut microbiome data further comprises
actual microbiome level; and
the user glycoprotein acetyls data further comprises
actual glycoprotein acetyls level.

15. The computer-implemented method of clause 12, wherein the time spent by the avatar in different health states further comprises:
total time spent by the avatar at the different stages of the digital vaccine environment,
total time spent by the avatar in a fit health state,
total time spent by the avatar in a danger health state, and
total time spent by the avatar in an unhealthy health state.

16. The computer-implemented method of clause 12, wherein the avatar's fitness further comprises:
avatar's movement speed.

17. The computer-implemented method of clause 12, wherein the parameters of the digital vaccine environment, the avatar, and the stages further comprise:
number of NPCs in the digital vaccine environment,
number of enemy NPCs in the digital vaccine environment,
strength of the enemy NPCs,
type of the enemy NPCs,
percentage of enemy NPCs,
type of friendly NPCs,
accuracy of enemy NPCs,
velocity of enemy NPCs,
virtual food spawn location,
levels and two-dimensional (2D) and three-dimensional augment reality and virtual reality assets selection, neurocognitive training module selection,
nutrition facts module,
game level up menu,
avatar mesh shape,
leaderboard on/off,
avatar powerup menu on/off,
avatar customization marketplace,
game feature reconfiguration setting,
level of virtual target selection,
level of real-world target selection, and
score target.

18. A non-transitory computer readable storage medium impressed with computer program instructions to provide a digital vaccine system, the instructions, when executed on a processor, implement a method comprising:
presenting a user-driven avatar with (i) tasks that test the avatar's physical fitness and (ii) food offerings at various stages, wherein the avatar's appearance is responsive to the avatar's performance on the tasks and selection of the food offerings;
monitoring the avatar's progression through the digital vaccine environment and producing avatar data, including (i) avatar food preference data, (ii) avatar calorie data, (iii) avatar insulin data, (iv) avatar glucose data, (v) avatar A1C data, and (vi) avatar ketone data, (vii) avatar cholesterol (HDL/LDL) data, (viii) avatar amino acid data, (ix) avatar glycoprotein acetyls data, and (x) avatar gut microbiome data and
accessing a user information database and producing user data, including (i) user food preference data, (ii) user calorie data, (iii) user glycemic data, (iv) user insulin data, (v) user glucose data, (vi) user A1C data, and (vii) user ketone data (viii) user cholesterol (HDL/LDL) data, (ix) user amino acid data, (x) user glycoprotein acetyls data, and (xi) user microbiome data;
processing (i) food logs, (ii) user conversation files, (iii) user images, and/or (iv) food images and producing nutrition data;
processing the avatar data, the user data, and the nutrition data and producing environment interaction data, including (i) metadata about the food offerings and the avatar's response to the food offerings, (ii) time spent by the avatar in different health states, and (iii) the avatar's fitness; and
modifying parameters of the digital vaccine environment, the avatar, and the stages based on the environment interaction data.

19. The non-transitory computer readable storage medium of clause 18, wherein the avatar's fitness further comprises:
avatar's movement speed.

20. The non-transitory computer readable storage medium of clause 18, wherein the parameters of the digital vaccine environment, the avatar, and the stages further comprise:
number of enemies in the digital vaccine environment,
number of enemy NPCs in the digital vaccine environment,
strength of the enemy NPCs,
type of the enemy NPCs,
percentage of enemy NPCs,
type of friendly NPCs,
accuracy of enemy NPCs,
velocity of enemy NPCs,
virtual food spawn location,
levels and two-dimensional (2D) and three-dimensional augment reality and virtual reality assets selection,
neurocognitive training module selection,
nutrition facts module,
game level up menu,
avatar mesh shape,
leaderboard on/off,
avatar powerup menu on/off,
avatar customization marketplace,
game feature reconfiguration setting,
level of virtual target selection,
level of real-world target selection, and
score target.

What is claimed is:

1. A digital vaccine system, comprising:
a digital vaccine environment, running on one or more hardware processors, which presents a user-driven avatar with (i) tasks that test the avatar's physical fitness and (ii) food offerings at various stages, wherein the avatar performs the tasks and selects the food offerings, and wherein the avatars appearance is responsive to the avatar's performance on the tasks and selection of the food offerings;
an input generation system with a virtual input generation sub-system and an actual input generation sub-system, wherein
the virtual input generation sub-system monitors the avatar's progression through the digital vaccine environment and produces avatar data, including (i) avatar food preference data, (ii) avatar calorie data, (iii) avatar insulin data, (iv) avatar glucose data, (v) avatar A1C data, (vi) avatar ketone data, (vii) avatar cholesterol (HDL/LDL) data, (viii) avatar amino acid data, (ix) avatar glycoprotein acetyls data, and (x) avatar gut microbiome data and
the actual input generation sub-system accesses a user information database and produces user data, including (i) user food preference data, (ii) user calorie data, (iii) user glycemic data, (iv) user insulin data, (v) user glucose data, (vi) user A1C data, (vii) user ketone data, (viii) user cholesterol (HDL/LDL) data, (ix) user amino acid data, (x) user glycoprotein acetyls data, and (xi) user microbiome data;
a nutrition data generation system that processes (i) food logs, (ii) user conversation files, (iii) user images, and/or (iv) food images and produces nutrition data;
a data processing system that processes the avatar data, the user data, and the nutrition data and produces environment interaction data, including (i) metadata about the food offerings and the avatars response to the food offerings, (ii) time spent by the avatar in different health states, and (iii) the avatar's fitness; and
a modification system that modifies parameters of the digital vaccine environment, the avatar, and the stages based on the environment interaction data.

2. The digital vaccine system of claim 1, wherein
the avatar food preference data further comprises
time stamped virtual food presented to the avatar in the digital vaccine environment, and
time stamped virtual food selected by the avatar in the digital vaccine environment;
the avatar calorie data further comprises
total calorie level of the avatar,
calories expanded by the avatar as a result of performing the tasks, and
net calorie level of the avatar;
the avatar insulin data further comprises
virtual insulin dose counter, and
virtual insulin units;
the avatar glucose data further comprises
virtual net blood glucose;

the avatar A1C data further comprises
  virtual A1C results;
the avatar ketone data further comprises
  virtual ketone level;
the avatar cholesterol data further comprises
  virtual LDL/HDL level;
the avatar amino acid data further comprises
  virtual amino acid level;
the avatar gut microbiome data further comprises
  virtual microbiome level; and
the avatar glycoprotein acetyl data further comprises
  virtual glycoprotein acetyls level.

3. The digital vaccine system of claim 1, wherein
the user food preference data further comprises
  time stamped actual food presented to the user in real world, and
  time stamped actual food consumed by the user in the real world;
the user calorie data further comprises
  actual calories consumed by the user in the real world, and
  calories expanded by the user in the real world;
the user glycemic data further comprises
  glycemic index, and
  glycemic load;
the user insulin data further comprises
  actual insulin dose counter, and
  actual insulin units;
the user glucose data further comprises
  actual net blood glucose;
the user A1C data further comprises
  actual Al C results;
the user ketone data further comprises
  actual ketone level;
the user cholesterol data further comprises
  actual LDL/HDL level;
the user amino acid data further comprises
  actual amino acid level;
the user gut microbiome data further comprises
  actual microbiome level; and
the user glycoprotein acetyls data further comprises
  actual glycoprotein acetyls level.

4. The digital vaccine system of claim 1, wherein the nutrition data generation system is a recurrent neural network that processes the user conversation files and produces the nutrition data.

5. The digital vaccine system of claim 1, wherein the nutrition data generation system is a convolutional neural network that processes the user images and/or the food images and produces the nutrition data.

6. The digital vaccine system of claim 1, wherein the nutrition data further comprises: amount of processed food servings,
  amount of natural food,
  amount of organic food,
  amount of genetically modified organism food,
  amount of net protein,
  amount of net carbohydrate,
  amount of net fat,
  amount of net transfat,
  amount of net saturated fat,
  amount of net high-density cholesterol,
  amount of net low-density cholesterol,
  amount of net vitamin A,
  amount of net vitamin B,
  amount of net vitamin C,
  amount of net vitamin D,
  amount of net vitamin E,
  amount of net iron,
  amount of net sodium,
  amount of net calcium,
  amount of net magnesium,
  amount of net potassium, and
  amount of net fiber.

7. The digital vaccine system of claim 1, wherein the metadata about the food offerings further comprises:
  frequency of food presented to the avatar in the digital vaccine environment,
  mathematical pattern of food choices presented to the avatar in the digital vaccine environment, and
  velocity of food choices presented to the avatar in the digital vaccine environment.

8. The digital vaccine system of claim 1, wherein the metadata about the avatar's response to the food offerings further comprises:
  number of interactions the avatar has with healthy food in the digital vaccine environment,
  number of interactions the avatar has with pseudo-healthy food in the digital vaccine environment,
  number of interactions the avatar has with unhealthy food in the digital vaccine environment,
  duration of the interactions, and
  velocity vector of the interactions.

9. The digital vaccine system of claim 1, wherein the time spent by the avatar in different health states further comprises:
  total time spent by the avatar at the different stages of the digital vaccine environment,
  total time spent by the avatar in a fit health state,
  total time spent by the avatar in a danger health state, and
  total time spent by the avatar in an unhealthy health state.

10. The digital vaccine system of claim 1, wherein the avatar's fitness further comprises:
  avatar's movement speed.

11. The digital vaccine system of claim 1, wherein the parameters of the digital vaccine environment, the avatar, and the stages further comprise:
  number of enemies in the digital vaccine environment,
  number of enemy Non player characters NPCs in the digital vaccine environment,
  strength of the enemy NPCs,
  type of the enemy NPCs,
  percentage of enemy NPCs,
  type of friendly NPCs,
  accuracy of enemy NPCs,
  accuracy of friendly NPCs
  velocity of NPCs,
  virtual food spawn location,
  levels and two-dimensional (2D) and three-dimensional augment reality and virtual reality assets selection,
  neurocognitive training module selection,
  nutrition facts module,
  game level up menu,
  avatar mesh shape,
  leaderboard on/off,
  avatar powerup menu on/off,
  avatar customization marketplace,
  game feature reconfiguration setting,
  level of virtual target selection,
  level of real-world target selection, and
  score target.

12. A computer-implemented method of providing a digital vaccine system, including:

presenting a user-driven avatar with (i) tasks that test the avatar's physical fitness and (ii) food offerings at various stages, wherein the avatar performs the tasks and selects the food offerings, and wherein the avatars appearance is responsive to the avatar's performance on the tasks and selection of the food offerings;

monitoring the avatar's progression through the digital vaccine environment and producing avatar data, including (i) avatar food preference data, (ii) avatar calorie data, (iii) avatar insulin data, (iv) avatar glucose data, (v) avatar Al C data, and (vi) avatar ketone data, (vii) avatar cholesterol (HDL/LDL) data, (viii) avatar amino acid data, (ix) avatar glycoprotein acetyls data, and (x) avatar gut microbiome data and accessing a user information database and producing user data, including (i) user food preference data, (ii) user calorie data, (iii) user glycemic data, (iv) user insulin data, (v) user glucose data, (vi) user A1C data, and (vii) user ketone data, (viii) user cholesterol (HDL/LDL) data, (ix) user amino acid data, (x) user glycoprotein acetyls data, and (xi) user microbiome data;

processing (i) food logs, (ii) user conversation files, (iii) user images, and/or (iv) food images and producing nutrition data;

processing the avatar data, the user data, and the nutrition data and producing environment interaction data, including (i) metadata about the food offerings and the avatar's response to the food offerings, (ii) time spent by the avatar in different health states, and (iii) the avatar's fitness; and modifying parameters of the digital vaccine environment, the avatar, and the stages based on the environment interaction data.

13. The computer-implemented method of claim 12, wherein
the avatar food preference data further comprises
time stamped virtual food presented to the avatar in the digital vaccine environment, and
time stamped virtual food selected by the avatar in the digital vaccine environment;
the avatar calorie data further comprises
total calorie level of the avatar,
calories expanded by the avatar as a result of performing the tasks, and
net calorie level of the avatar;
the avatar insulin data further comprises
virtual insulin dose counter, and
virtual insulin units;
the avatar glucose data further comprises
virtual net blood glucose;
the avatar A1C data further comprises
virtual A1C results;
the avatar ketone data further comprises
virtual ketone level;
the avatar cholesterol data further comprises
virtual LDL/HDL level;
the avatar amino acid data further comprises
virtual amino acid level;
the avatar gut microbiome data further comprises
virtual microbiome level; and
the avatar glycoprotein acetyl data further comprises
virtual glycoprotein acetyls level.

14. The computer-implemented method of claim 12, wherein the user food preference data further comprises
time stamped actual food presented to the user in real world, and
time stamped actual food consumed by the user in the real world;
the user calorie data further comprises
actual calories consumed by the user in the real world,
calories expanded by the user in the real world;
the user glycemic data further comprises
glycemic index, and
glycemic load;
the user insulin data further comprises
actual insulin dose counter, and
actual insulin units;
the user glucose data further comprises
actual net blood glucose;
the user A1C data further comprises
actual Al C results;
the user ketone data further comprises
actual ketone level;
the user cholesterol data further comprises
actual LDL/HDL level;
the user amino acid data further comprises
actual amino acid level;
the user gut microbiome data further comprises
actual microbiome level; and
the user glycoprotein acetyls data further comprises
actual glycoprotein acetyls level.

15. The computer-implemented method of claim 12, wherein the time spent by the avatar in different health states further comprises:
total time spent by the avatar at the different stages of the digital vaccine environment,
total time spent by the avatar in a fit health state,
total time spent by the avatar in a danger health state, and
total time spent by the avatar in an unhealthy health state.

16. The computer-implemented method of claim 12, wherein the avatar's fitness further comprises:
avatar's movement speed.

17. The computer-implemented method of claim 12, wherein the parameters of the digital vaccine environment, the avatar, and the stages further comprise:
number of NPCs in the digital vaccine environment,
number of enemy NPCs in the digital vaccine environment,
strength of the enemy NPCs,
type of the enemy NPCs,
percentage of enemy NPCs,
type of friendly NPCs,
accuracy of enemy NPCs,
velocity of enemy NPCs,
virtual food spawn location,
levels and two-dimensional (2D) and three-dimensional augment reality and virtual reality assets selection,
neurocognitive training module selection,
nutrition facts module,
game level up menu,
avatar mesh shape,
leaderboard on/off,
avatar powerup menu on/off,
avatar customization marketplace,
game feature reconfiguration setting,
level of virtual target selection,
level of real-world target selection, and
score target.

18. A non-transitory computer readable storage medium impressed with computer program instructions to provide a digital vaccine system, the instructions, when executed on a processor, implement a method comprising:

presenting a user-driven avatar with (i) tasks that test the avatar's physical fitness and (ii) food offerings at various stages, wherein the avatar performs the tasks and selects the food offerings, and wherein the avatars appearance is responsive to the avatar's performance on the tasks and selection of the food offerings;

monitoring the avatar's progression through the digital vaccine environment and producing avatar data, including (i) avatar food preference data, (ii) avatar calorie data, (iii) avatar insulin data, (iv) avatar glucose data, (v) avatar Al C data, and (vi) avatar ketone data, (vii) avatar cholesterol (HDL/LDL) data, (viii) avatar amino acid data, (ix) avatar glycoprotein acetyls data, and (x) avatar gut microbiome data and accessing a user information database and producing user data, including (i) user food preference data, (ii) user calorie data, (iii) user glycemic data, (iv) user insulin data, (v) user glucose data, (vi) user A1C data, and (vii) user ketone data (viii) user cholesterol (HDL/LLDL) data, (ix) user amino acid data, (x) user glycoprotein acetyls data, and (xi) user microbiome data;

processing (i) food logs, (ii) user conversation files, (iii) user images, and/or (iv) food images and producing nutrition data;

processing the avatar data, the user data, and the nutrition data and producing environment interaction data, including (i) metadata about the food offerings and the avatar's response to the food offerings, (ii) time spent by the avatar in different health states, and (iii) the avatar's fitness; and modifying parameters of the digital vaccine environment, the avatar, and the stages based on the environment interaction data.

19. The non-transitory computer readable storage medium of claim 18, wherein the avatar's fitness further comprises:
avatar's movement speed.

20. The non-transitory computer readable storage medium of claim 18, wherein the parameters of the digital vaccine environment, the avatar, and the stages further comprise:
number of enemies in the digital vaccine environment,
number of enemy NPCs in the digital vaccine environment,
strength of the enemy NPCs,
type of the enemy NPCs,
percentage of enemy NPCs,
type of friendly NPCs,
accuracy of enemy NPCs,
velocity of enemy NPCs,
virtual food spawn location,
levels and two-dimensional (2D) and three-dimensional augment reality and virtual reality assets selection,
neurocognitive training module selection,
nutrition facts module,
game level up menu,
avatar mesh shape,
leaderboard on/off,
avatar powerup menu on/off,
avatar customization marketplace,
game feature reconfiguration setting,
level of virtual target selection,
level of real-world target selection, and
score target.

* * * * *